(12) United States Patent
Kraz et al.

(10) Patent No.: US 7,085,120 B2
(45) Date of Patent: Aug. 1, 2006

(54) SELF-DISENGAGING WEARABLE GROUNDING DEVICE

(75) Inventors: Vladimir Kraz, Santa Cruz, CA (US);
Kirk Alan Martin, Aptos, CA (US);
Fatjon Gurga, San Jose, CA (US);
Yelena Kraz, Santa Cruz, CA (US)

(73) Assignee: Credence Technologies, Inc., Soquel, CA (US)

( * ) Notice: Subject to any disclaimer, the term of this patent is extended or adjusted under 35 U.S.C. 154(b) by 515 days.

(21) Appl. No.: 10/434,765

(22) Filed: May 8, 2003

(65) Prior Publication Data

US 2004/0196612 A1   Oct. 7, 2004

Related U.S. Application Data

(60) Provisional application No. 60/460,356, filed on Apr. 3, 2003.

(51) Int. Cl.
*H02H 3/00* (2006.01)

(52) U.S. Cl. .................................. 361/220

(58) Field of Classification Search ............. 361/216, 361/220, 232
See application file for complete search history.

(56) References Cited

U.S. PATENT DOCUMENTS

| 3,857,397 | A | * | 12/1974 | Brosseau ............... 607/149 |
| 4,638,399 | A | * | 1/1987 | Maroney et al. ......... 361/220 |
| 4,710,751 | A | * | 12/1987 | Webster ................ 340/522 |
| 4,868,710 | A | * | 9/1989 | Powell ................. 361/212 |
| 4,974,594 | A | * | 12/1990 | Berlin ................. 600/395 |
| 5,004,425 | A | * | 4/1991 | Hee ..................... 439/37 |
| 6,866,128 | B1 | * | 3/2005 | Moore et al. .......... 191/12.4 |

* cited by examiner

*Primary Examiner*—Ronald Leja
(74) *Attorney, Agent, or Firm*—DLA Piper Rudnick Gray Cary US LLP

(57) ABSTRACT

The invention is a grounding device that grounds the wearer when the wearer is in a designated area and automatically disengages when the wearer leaves the designated area. In more detail, the grounding device includes a wristband that is electrically coupled to a grounded object with a fastening mechanism, wherein the fastening mechanism automatically releases to separate the wristband from the grounded object if the wristband is outside of the designated area. Where the fastening mechanism includes a coupling mechanism (e.g., a wire), there may be a rotating device that retracts the coupling mechanism after the fastening mechanism is released. The device may be enhanced with a grounding device monitoring unit that monitors whether the grounding device is in use and a sensor that detects whether the operator is in the designated area, so that an alarm is triggered if the operator is in the designated area and the grounding device is not in use.

55 Claims, 17 Drawing Sheets

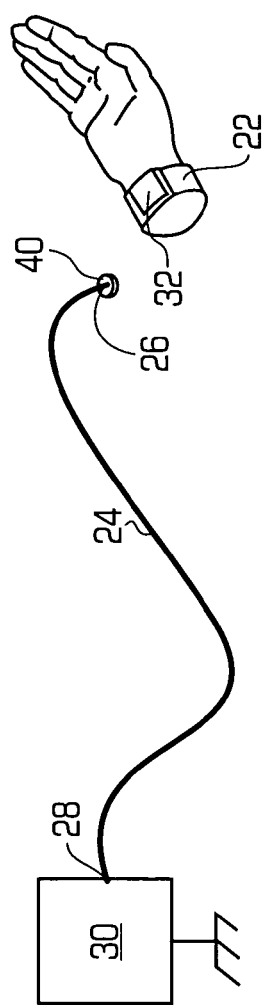
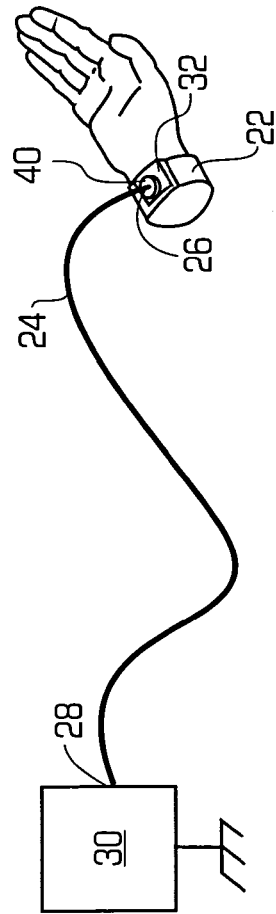
FIG. 2a
FIG. 2b

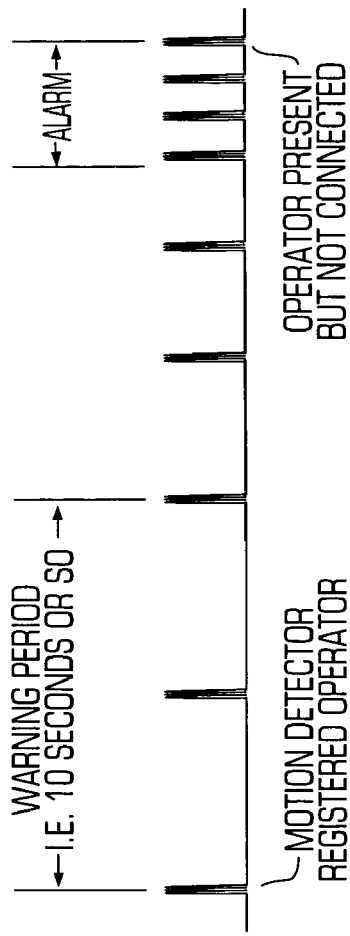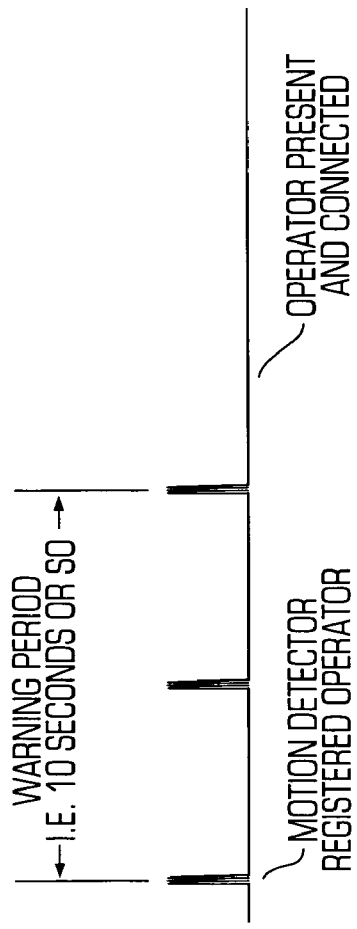

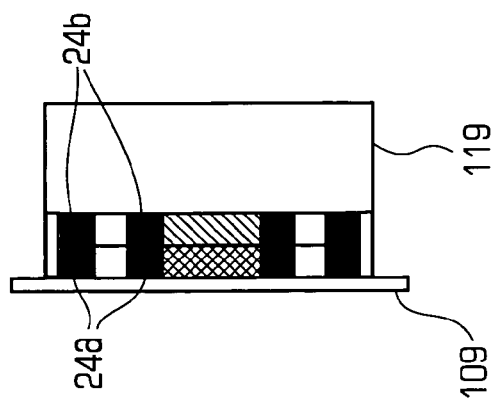
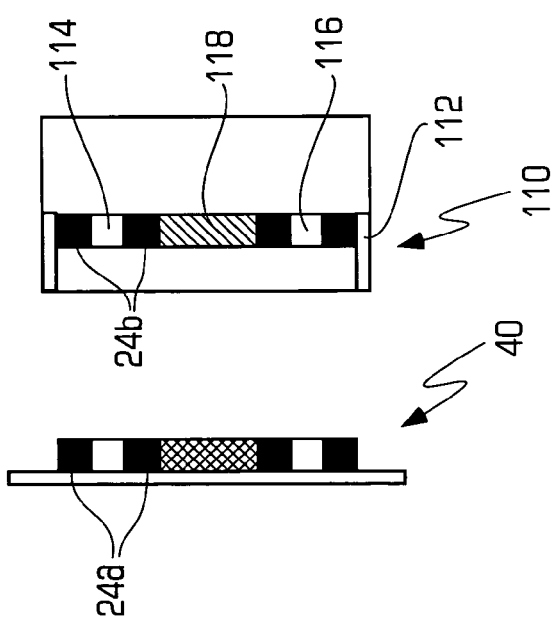
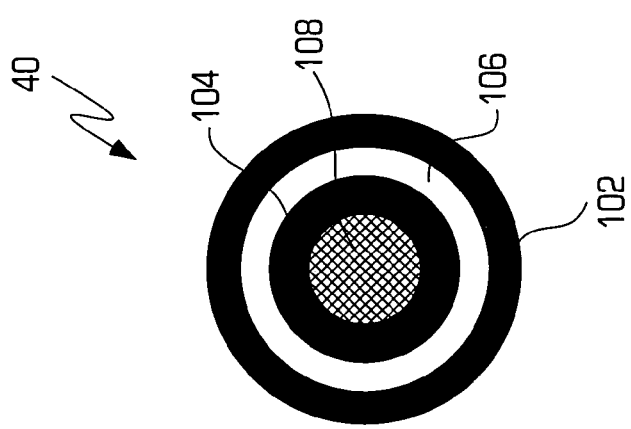
FIG. 14c
FIG. 14b
FIG. 14a

SELF-DISENGAGING WEARABLE GROUNDING DEVICE

RELATED APPLICATION

This application claims the benefit under 35 U.S.C. § 119(e) of U.S. Provisional Application No. 60/460,356 filed on Apr. 3, 2003, which is incorporated herein by reference in its entirety.

FIELD OF THE INVENTION

The invention relates generally to a device, system, and method for grounding a user to prevent electrostatic discharge and in particular to a device, system, and method for a self-disengaging grounding device.

BACKGROUND OF THE INVENTION

It is well known that when operating equipment or a component that is sensitive to electrostatic discharge, operators must be grounded to prevent electrostatic damage to the sensitive equipment/component. Guidelines such as ANSI/ESDA S.20.20 standards (available at www.esda.org) provide requirements for operators to be grounded. These guidelines are typically met by requiring each operator to wear a wristband that is electrically connected to a grounding jack. Although the grounded wristband method seems like a sound solution in theory, it has proven to be highly unreliable in practice. Many operators do not follow the manufacturing procedure that requires them to wear the grounded wristbands because connecting the wristbands to the grounding jack is an inconvenient process, the wire that connects the wristband to the grounding jack interferes with movement, or because the operators forget to put them on. Sometimes, an operator mistakenly believes that he is grounded after putting on a wristband when in fact, the wristband is not securely connected to the grounding jack. For example, the wristband is sometimes worn over the operator's sleeve, making no direct connection to the operator. Due to the low reliability of the current wristband-based grounding system, many expensive manufacturing equipment continue to be damaged or destroyed by electrostatic discharge.

As mentioned above, one of the reasons operators fail to be properly grounded is because the process of connecting the wristband to the grounding jack is cumbersome, complicated, and/or inconvenient. Since operators are required to connect the wristband to the grounding jack every time they approach the sensitive equipment/component, and to disconnect the wristband every time they move away from the equipment/component, they often have to connect and disconnect their wristband numerous times in one day. Thus, any process but a very simple and quick connection/disconnection process becomes burdensome.

It is just as important for the operator to disconnect himself when leaving the designated area as for him to connect himself upon entering the designated area. If an operator leaves the equipment without disconnecting the wristband from the grounding jack, the connection wire may get stretched beyond its acceptable tension level and become damaged. The connectors that connect the wire to the grounding jack may also become damaged.

For the above reasons, a more reliable grounding system and method are desired. In order to be more reliable, the grounding system has to provide a quick and easy way for operators to ground/de-ground themselves and reduce the chances that an operator will forget to ground/de-ground himself as is appropriate.

SUMMARY OF THE INVENTION

The invention pertains to a device, system, and method for grounding an operator such that it takes minimal effort on the part of the operator to get grounded. The invention provides the added benefit of automatically disengaging if the operator leaves a designated area, so that the operator does not have to remember to disconnect himself from the grounding device.

The invention is a wearable grounding device that grounds the wearer when the wearer is in a designated area and automatically disengages when the wearer leaves the designated area. In more detail, the grounding device includes a wristband that is electrically coupled to a grounded object with a fastening mechanism, wherein the fastening mechanism automatically releases to separate the wristband from the grounded object if the wristband is outside of the designated area. Where the fastening mechanism includes a coupling mechanism (e.g., a wire), there may be a rotating device that retracts the coupling mechanism after the fastening mechanism is released.

To further foolproof the device, the device may be enhanced with a grounding device monitoring unit that monitors whether the grounding device is in use or not. This grounding device monitoring unit may be used in conjunction with a sensor that detects whether the operator is in the designated area so that an alarm is triggered if the operator is in the designated area and the grounding device is not in use. Instead of or in addition to triggering the alarm, equipment that is sensitive to electrostatic discharge may be automatically disabled if the operator is in the designated area without using the grounding device.

BRIEF DESCRIPTION OF THE DRAWINGS

FIGS. 2a–2d depict another magnetic embodiment of the grounding device in accordance with the invention;

FIGS. 9c and 9d depict alarm signal intensity as a function of time;

FIGS. 14a–14c shows an embodiment of a magnetic mating structure in accordance with the invention;

DETAILED DESCRIPTION OF A PREFERRED EMBODIMENT

Figure 1A:
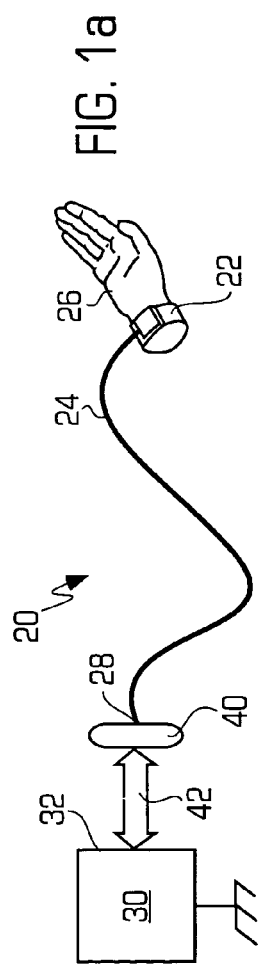
FIGS. 1a–1d depict a magnetic embodiment of the grounding device in accordance with the invention.

The invention is particularly applicable to a user grounding system and it is in this context that the invention will be described. It will be appreciated, however, that the device and method in accordance with the invention has greater utility.

As used herein, a "designated area" is an area where an operator is required to be grounded, such as a workbench, the vicinity of a sensitive equipment, or a manufacturing area. Also, as used herein, the "first end" is the end of a coupling mechanism that is near the wristband worn by the operator and the "second end" is the end of the coupling mechanism that is near the grounded object. A "coupling mechanism" is a device, mechanism, or system for electrically coupling two points, including but not limited to a conventional cable, a metallic wire, a conductive wire, a conductive fabric, a synthetic wire/tape, or an insulative cord/tape that has a woven conductive strand. A "wristband" is any type of object that is shaped to be worn by a person and makes electrical contact with the person. A "fastening mechanism" is any device, mechanism, or system of electrically coupling the wristband to a grounded object in a releasable manner by coupling a mating structure with a fixing mechanism.

FIGS. 1a–1d, 2a–2d, 3a, 3b, and 4a–4d depict different embodiments of a grounding device 20 in accordance with the invention. The grounding device 20 includes a wristband 22 that is electrically coupled to a grounded object 30 with a self-disengaging fastening mechanism. The fastening mechanism includes a coupling mechanism 24 that securely connects the wristband 22 to the grounded object 30 and automatically disconnects the wristband 22 and/or the coupling mechanism from the grounded object 30 when the tension level of the coupling mechanism exceeds a threshold level, to prevent damage to the component that is being operated on. This secure connection is achieved by coupling a mating structure (e.g., a magnetic mating structure 40 or a mechanical mating structure 54 described below) with a fixing mechanism (e.g., a ferromagnetic fixing mechanism 30 or a mechanical fixing mechanism 52). The fixing mechanism is designed to release the mating structure in response to a certain level of force being applied to the mating structure. The mating structure and the fixing mechanism may use any conventional mechanism for releasably coupling two objects.

FIGS. 1a, 1b, 1c, and 1d depict a magnetic embodiment of the grounding device 20 in accordance with the invention. FIG. 1a depicts a first magnetic embodiment of the grounding device 20. In this embodiment, a first end 26 of the coupling mechanism 24 is connected to the wristband 22 and a second end 28 of the coupling mechanism 24 is connected to a magnetic mating structure 40 that is designed to be releasably coupled to the grounded object 30. The grounded object 30, in this embodiment, has a ferromagnetic fixing mechanism 32 to which the magnetic mating structure 40 can securely but releasably attach. The size of the magnetic mating structure 40 is controlled so that a moderate amount of tugging on the coupling mechanism 24 will cause it to detach from the ferromagnetic fixing mechanism 32, as indicated by an arrow 42. This way, if an operator forgets to disconnect the wristband 22 from the grounded object 30 before leaving the designated area, the magnetic mating structure 40 will self-disengage from the ferromagnetic fixing mechanism 32 when the coupling mechanism has a predetermined pulling force applied to it, such as when the operator is a certain distance away from the grounded object 30. A person of ordinary skill in the art would understand to set the length of the coupling mechanism 24 such that the magnetic mating structure 40 will not self-disengage when the operator is still in the designated area.

Figure 1B:
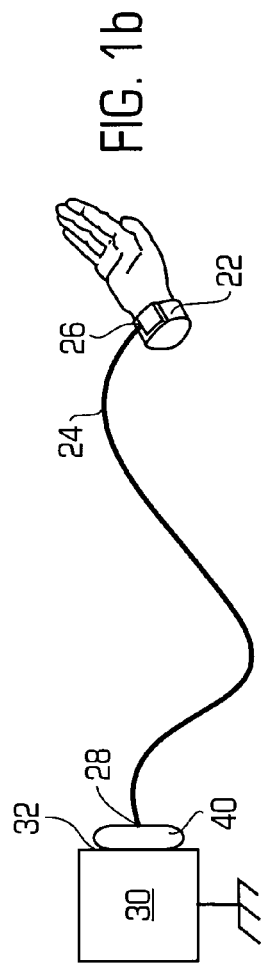

FIG. 1b depicts the magnetic embodiment of FIG. 1a when the magnetic mating structure 40 is attached to the ferromagnetic fixing mechanism 32 so that the user is grounded.

Figure 1C:
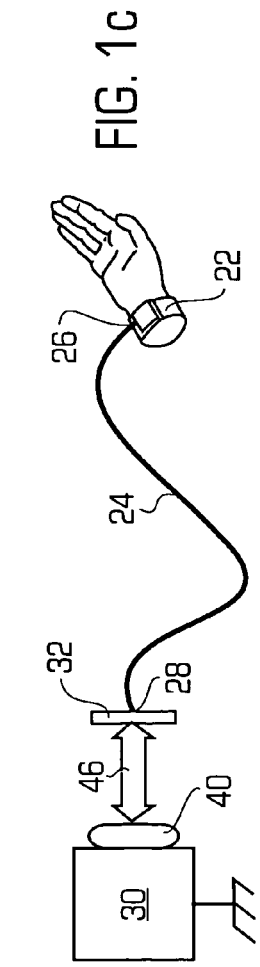
Figure 1D:
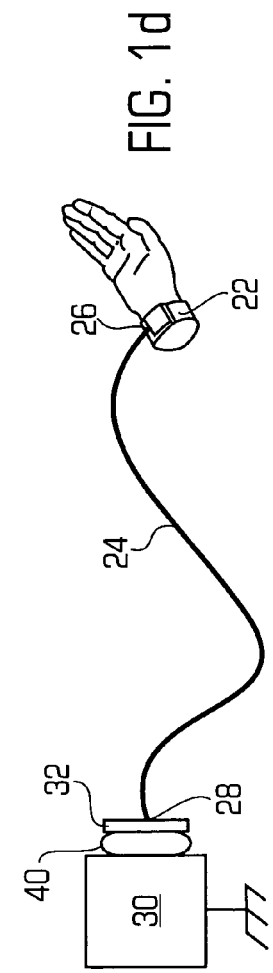

FIGS. 1c and 1d depict an alternative magnetic embodiment of the grounding device 20 in accordance with the invention. In this alternative embodiment, the positions of the ferromagnetic metal surface 32 and the magnetic mating structure 40 are changed relative to the embodiment in FIGS. 1a and 1b. Instead of the second end 28 of the coupling mechanism 24 being connected to the magnetic mating structure 40, it is connected to the ferromagnetic fixing mechanism 32. In this embodiment, the grounded object 30 includes the magnetic mating structure 40 that is positioned to be coupled with the ferromagnetic fixing mechanism 32, as shown in FIG. 1d. When an operator wearing the wristband 22 travels beyond the length of the coupling mechanism 24 or exerts a particular predetermined force on the coupling mechanism 24, the ferromagnetic fixing mechanism 32 automatically disengages from the magnet 48, as indicated by an arrow 46 (in FIG. 1c). A person of ordinary skill in the art would understand how to design such arrangements. This alternative embodiment of FIGS. 1c and 1d may be preferable to the embodiment of FIG. 1a and 1b if the presence of a magnet at the end of the coupling mechanism 24 is not desirable due to certain manufacturing conditions.

Figure 1E:
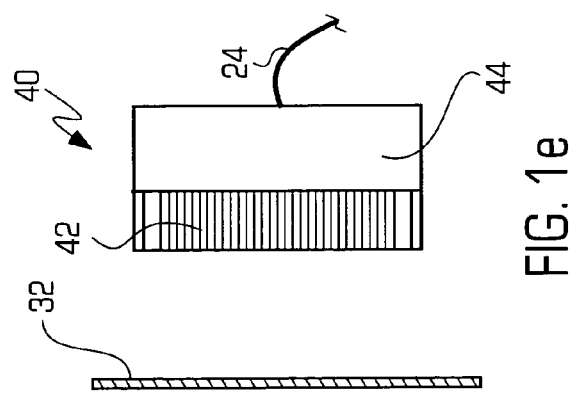
FIG. 1e depicts an embodiment of the magnetic device in accordance with the invention.

FIG. 1e depicts an embodiment of the magnetic mating structure 40 in accordance with the invention. In the embodiments of FIGS. 1a, 1b, 1c, and 1d, the magnetic mating structure 40 has to be both magnetic and electrically conductive. This can be achieved by using a material that is both magnetic and electrically conductive, or by mounting a magnetic material on an electrically conductive arrangement. If the magnetic mating structure 40 includes a magnetic material that is also electrically conductive, the magnetic material can be designed as part of the electrical connection. On the other hand, if the magnetic mating structure 40 includes a nonconductive magnetic material 42 (e.g., ceramics), the magnetic mating structure 40 may also include a metal casing or shell 44 to establish electrical connection between the coupling mechanism 24 and the ferromagnetic fixing mechanism 32.

The grounding of the operator does not require low resistance nor high current capacity. Therefore, it is possible to use more flexible and easily extendable material for the coupling mechanism 24 that would further improve convenience for operators and facilitate proper grounding.

FIGS. 2a–2d show yet another magnetic embodiment in accordance with the invention. Unlike in the embodiments of FIGS. 1a–1d, where the releasable attachment of the coupling mechanism 24 occurred near the second end 28 of the coupling mechanism 24, the releasable attachment occurs at the first end 26 in the embodiments of FIGS. 2a–2d. As in the embodiments of FIGS. 1a–1d, the magnetic mating structure 40 is both magnetic and electrically conductive. The embodiments of FIGS. 2a–2d may be preferred over the embodiments of FIGS. 1a–1d because the operator would not carry/drag around the coupling mechanism 24 upon leaving the designated area.

In the embodiment of FIGS. 2a and 2b, the first end 26 of the coupling mechanism 24 is connected to the magnetic mating structure 40 and the second end 28 is connected to the grounded object 30. In this embodiment, the wristband 22 has the ferromagnetic fixing mechanism 32 attached to it so that it can connect to the coupling mechanism 24 via the magnetic mating structure 40 as shown in FIG. 2b.

Figure 2C:
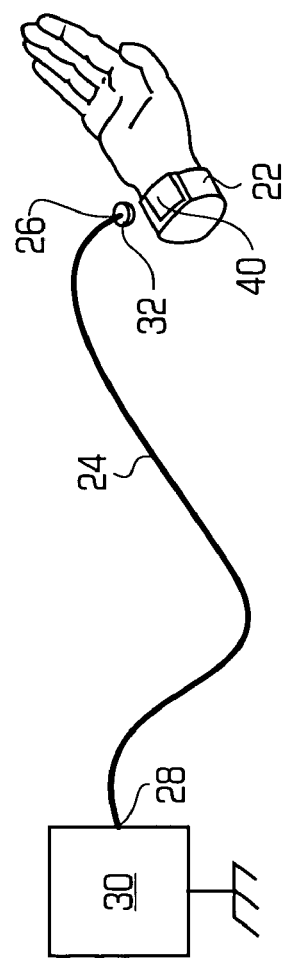
Figure 2D:
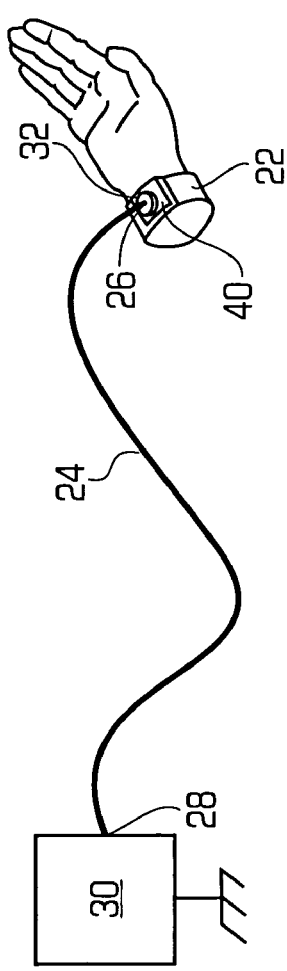

The embodiment of FIGS. 2c and 2d is similar to the embodiment of FIGS. 2a and 2b except that the positions of the ferromagnetic fixing mechanism 32 and the magnetic mating structure 40 are changed. In the embodiment of FIGS. 2c and 2d, the first end 26 of the coupling mechanism 24 is connected to the ferromagnetic fixing mechanism 32 and the second end 28 is connected to the grounded object 30. The wristband 22 includes the magnetic mating structure 40 that couples to the ferromagnetic fixing mechanism 32, as shown in FIG. 2d.

Figure 3A:
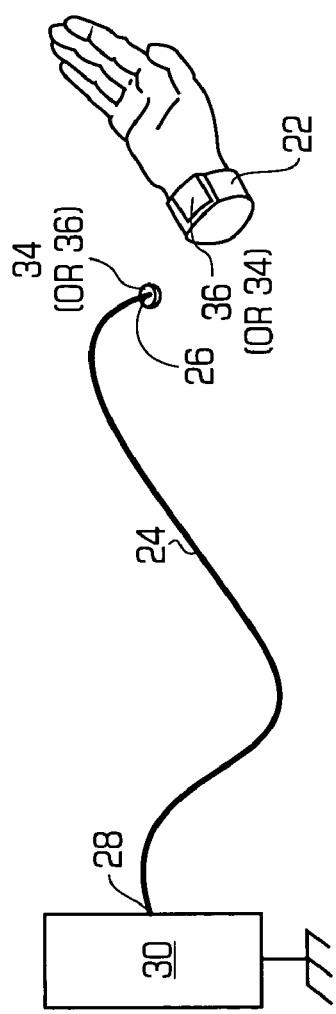
FIGS. 3a and 3b depict a Velcro-type embodiment of the grounding device in accordance with the invention.
Figure 3B:
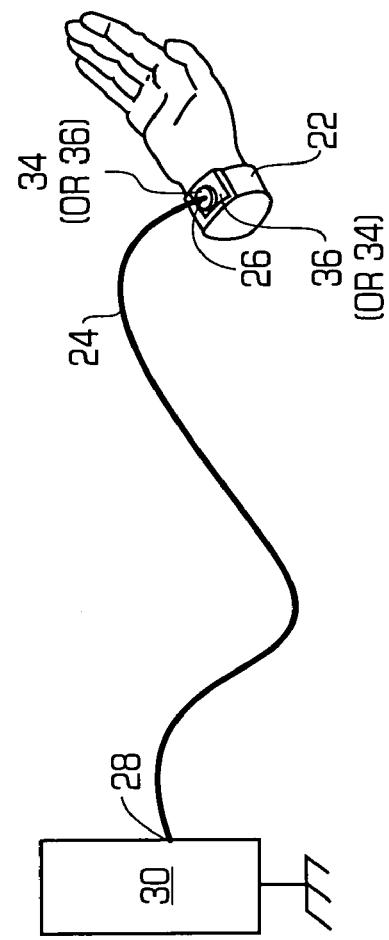

FIGS. 3a and 3b depict a Velcro-type embodiment of the grounding device 20 in accordance with the invention. This Velcro-type embodiment is similar to the magnetic embodiment described above except that a Velcro is used as the fastening mechanism instead of the magnetic mating structure 40 and the ferromagnetic fixing mechanism 32. The Velcro-based fastening mechanism includes a loop-type mating structure 34 and a hook-type fixing mechanism 36, as shown in FIGS. 3a and 3b. The Velcro that is used herein has a conductive portion to allow proper grounding of the wristband 22. The Duo-lock type fastening mechanism (manufactured by 3M Corporation) may be used. As indicated in parenthesis, the positions of the loop-type mating structure 34 and the hook-type fixing mechanism 36 may be switched.

Figure 4B:
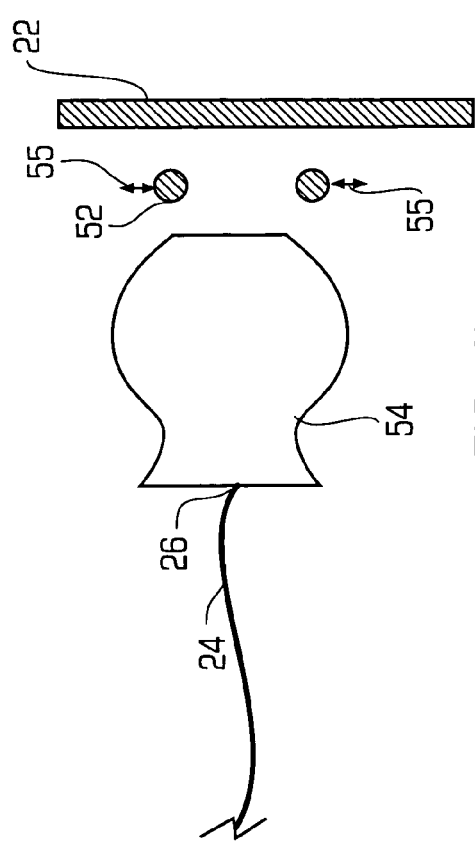
FIGS. 4a–4d depict a mechanical embodiment of the grounding device in accordance with the invention.
Figure 4D:
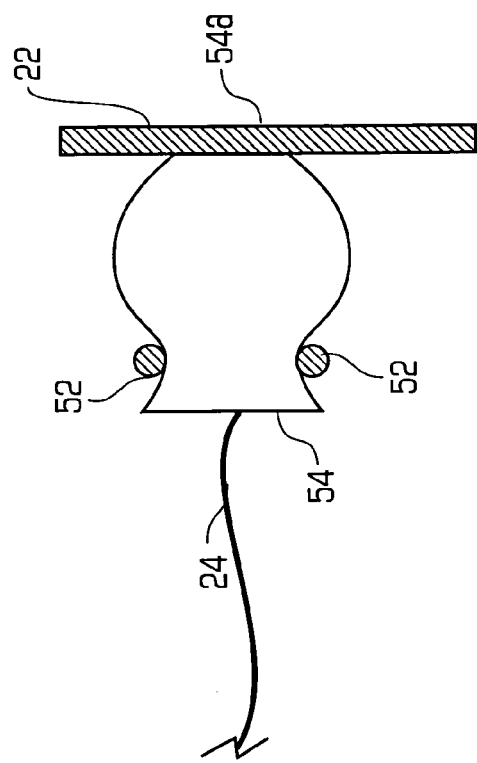
Figure 4A:
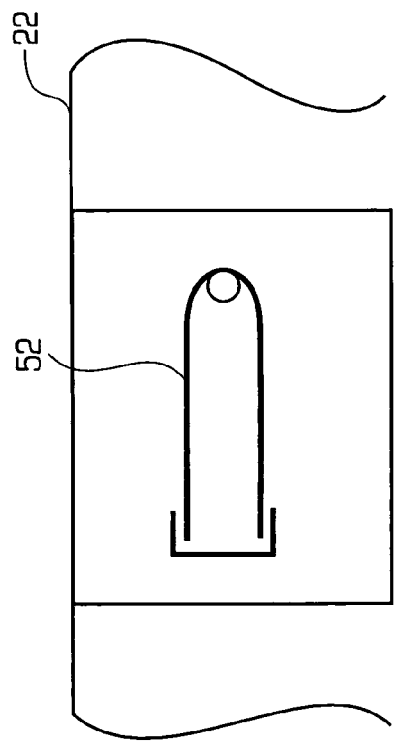
Figure 4C:
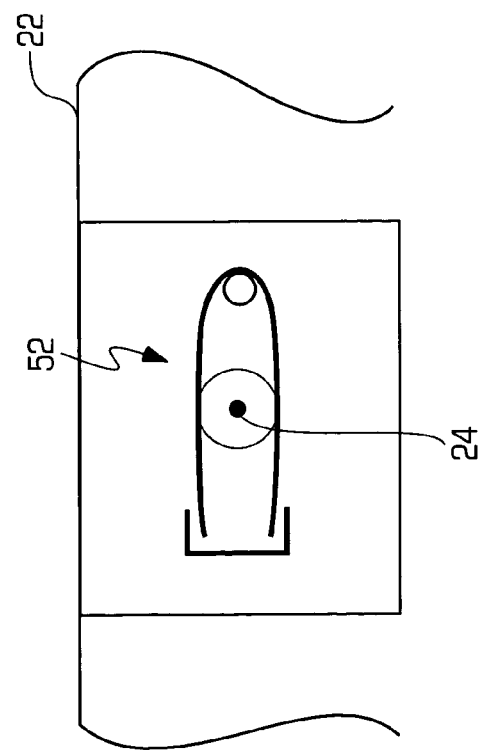

FIGS. 4a, 4b, 4c, and 4d depict a mechanical embodiment of the grounding device 20 in accordance with the invention. FIGS. 4a and 4c are top views and FIGS. 4b and 4d are side views. The mechanical embodiment achieves the same function as the magnetic embodiment, but without using magnetic material. Instead of using the magnetic mating structure 40 and the ferromagnetic fixing mechanism 32, the mechanical embodiment utilizes a mechanical mating structure 54 and a mechanical fixing mechanism 52. FIG. 4a shows an exemplary fixing mechanism 52 attached to a wristband 22. The mechanical fixing mechanism 52 is any type of mechanism that would hold the mechanical mating structure 54 in place and release it in response to a pulling force. For example, the mechanical fixing mechanism 52 may include a spring-loaded contact so that the mechanical mating structure 54 can be inserted or withdrawn as the spring-loaded contact moves in the directions shown by arrows 55. The mechanical mating structure 54 is connected to the first end 26 of the coupling mechanism 24. The mechanical mating structure 54 either has an electrically conductive section 54a or accommodates the coupling mechanism 24 so that the coupling mechanism 24 mates with the electrically conductive portions of the wristband 22 when the mechanical mating structure 54 is held by the mechanical fixing mechanism 52. The mechanical mating structure 54 is shaped to easily and securely become engaged with the wristband 22 (see FIGS. 4c and 4d) while becoming disengaged from the spring-loaded contact by a moderate amount of pulling.

The embodiments described in FIGS. 1a–1d, 2a–2d, and 4a–4d provide a way of easily and securely coupling the wristband 22 to the grounded object 30 in a way that also allows decoupling when a sufficient force is applied to the coupling mechanism 24, for example if the wristband 22 and the grounded object 30 are separated by a distance longer than the length of the coupling mechanism 24. A minimal effort is needed on the part of the operator to become grounded (i.e., couple the wristband 22 to the grounded object 30), and no effort is needed to disengage the ground connection when the operator leaves the designated area since the wristband 22 and the grounded object 30 are releasably coupled.

After the fastening mechanism disengages to decouple the wristband 22 from the grounded object 30, the coupling mechanism 24 could be left lying on the floor or be dragged around by the operator, interfering with foot traffic and possibly causing a dangerous situation. FIG. 5a depicts a spring-loaded spool 70 that may be used to automatically retract the coupling mechanism 24 after the grounding device 20 is disengaged from the grounded object 30. The spring-loaded spool 70 may be designed to maintain a comfortable level of tension in the coupling mechanism 24 when the wearer of the wristband 22 walks around, so that when the tension level drops due to either the disengagement of the wristband 22 from the grounded object 30 or the discontinued use of the wristband 22 by the operator, the spool is triggered automatically to retract the coupling mechanism 24. Optionally, a well-known ratchet mechanism (not shown) may be incorporated into the spool 70 to hold the coupling mechanism 24 in the extended state so that the operator is not constantly pulled by the spring-loaded spool 70. This spring-loaded spool 70 may be used for any embodiment of the grounding device 20 described above.

Figure 5B:
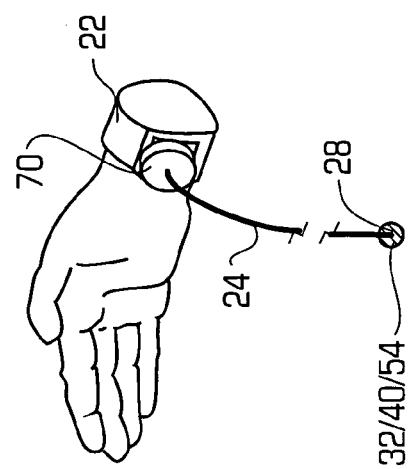
FIGS. 5a and 5b depicts a spring-loaded spool that may be used to automatically retract the coupling mechanism after the grounding device is disengaged from the grounded object.
Figure 5A:
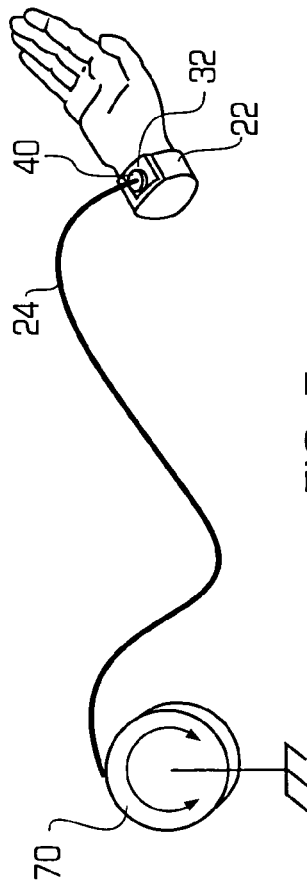

FIG. 5b depicts an embodiment of the grounding device 20 wherein the spool 70 is attached to the first end 26 of the coupling mechanism 24 instead of the second end 28. As shown, the spring-loaded spool 70 may be attached to the wristband 22. A mating structure such as a magnetic mating structure 40 or a mechanical mating structure 54 may be attached to the second end 28 of the coupling mechanism 24. Alternatively, a fixing mechanism such as a ferromagnetic fixing mechanism 32 may be attached to the second end 28.

Figure 6B:
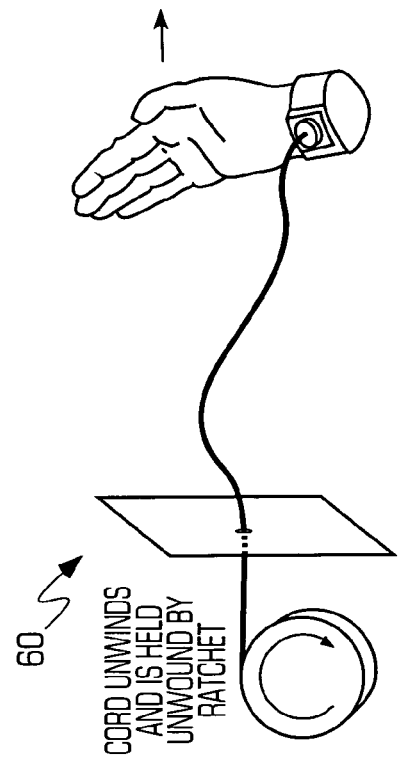
FIGS. 6a and 6c depict a grounding system including the spring-loaded spool of FIG. 5a and the grounding device of FIGS. 2a and 2b.
Figure 6A:
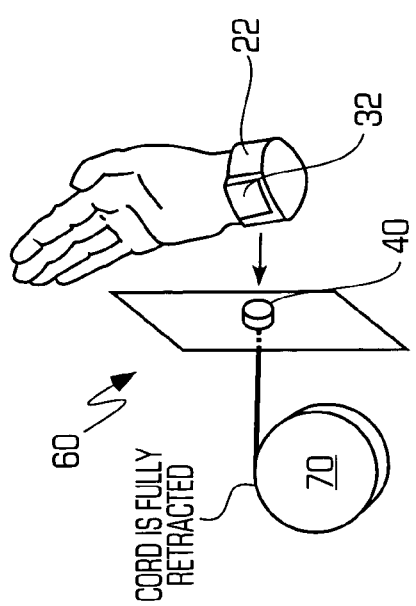
Figure 6C:
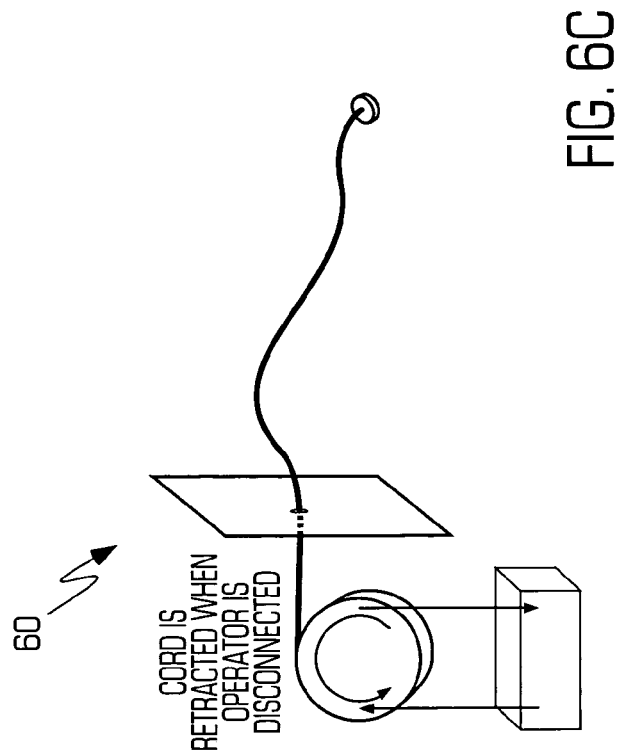

FIGS. 6a–6c depict a grounding system 60 including the spring-loaded spool 70 of FIG. 5a and the grounding device 20 of FIGS. 2a and 2b. An operator grounds himself by putting on the wristband 22 and touching the magnetic mating structure 40 with the ferromagnetic fixing mechanism 32 on his wristband 22. When the operator moves away from the spring-loaded spool 70, the coupling mechanism 24 is automatically extended to allow unrestricted movement for the operator, as shown in FIG. 6b. After the operator disengages from the cable 24, the coupling mechanism 24 is retracted in by the spring-loaded spool 70, as shown in FIG. 6c. The invention is not limited to a specific way in which the retraction of the coupling mechanism 24 is triggered. For example, if the spring-loaded spool 70 is designed to maintain a constant level of tension in the coupling mechanism 24 as mentioned above, the retraction will automatically happen when the fastening mechanism is disengaged. Alternatively, the retraction may be triggered by the operator's sharply tugging the coupling mechanism 24 to release a latch. If a ratchet mechanism is used, a detector circuit may be used to release the ratchet latch that was holding the coupling mechanism 24 in its extended position. A circuit may be used to detect that the fastening mechanism is disengaged and activate an electric motor to retract the cable 24.

Figure 7:
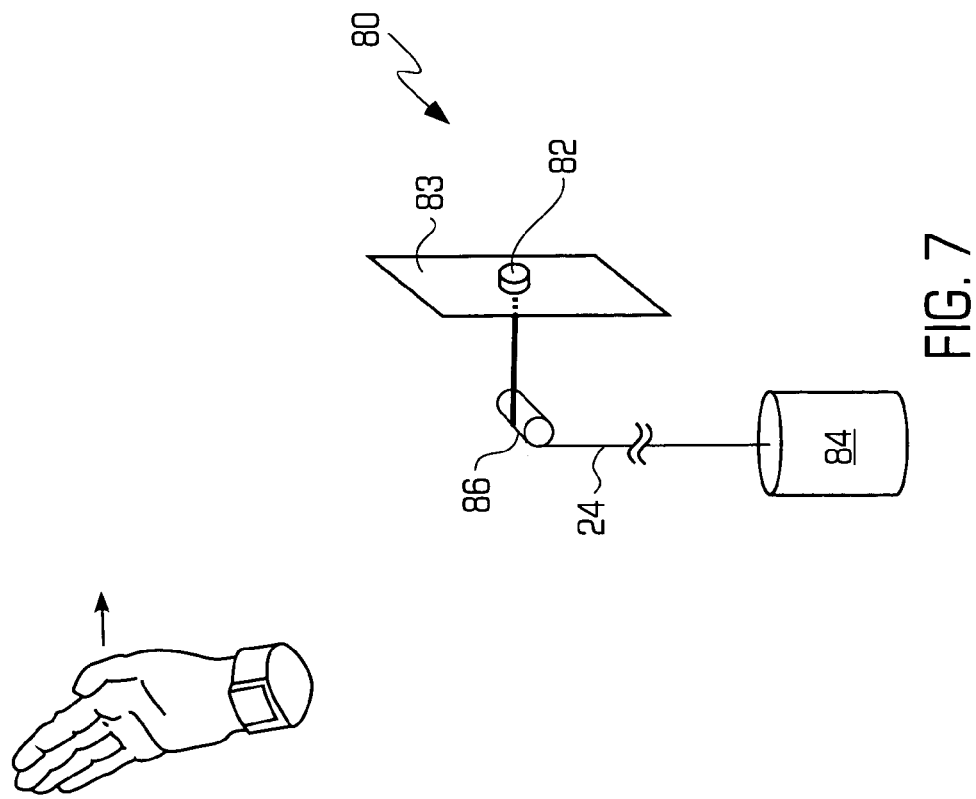
FIG. 7 depicts a weighted retraction system in accordance with the invention.

FIG. 7 depicts a weighted retraction system 80 that may be used instead of or in combination with the spring-loaded spool 70 to handle the coupling mechanism 24 when the grounding device 20 is not in use. The weighted retraction system 80 includes a weight 84 connected to one end of the coupling mechanism 24 and a pulley 86 that controls the position of the weight 84. The pulley effectively translates the vertical motion of the weight 84 into a horizontal force that pulls in the coupling mechanism 24. Once the fastening mechanism is disengaged, the retraction may continue until a stopper 82 (which may be, for example, the magnetic mating structure 40) comes in contact with a plate 83 through which the coupling mechanism 24 extends. The plate 83 may be grounded. The weighted retraction system 80 may be used with the embodiments of FIGS. 2a–2d where the detachment occurs at the first end 26 of the coupling mechanism 24. A person of ordinary skill in the art would understand to adjust the weight 84 so that it is not too heavy for the wearer while the grounding device 20 is in use.

The abovementioned methods and devices for retracting the coupling mechanism 24 may also be accomplished using gravity-driven retraction mechanisms or electric drive (i.e., motor) based mechanisms.

Figure 8:
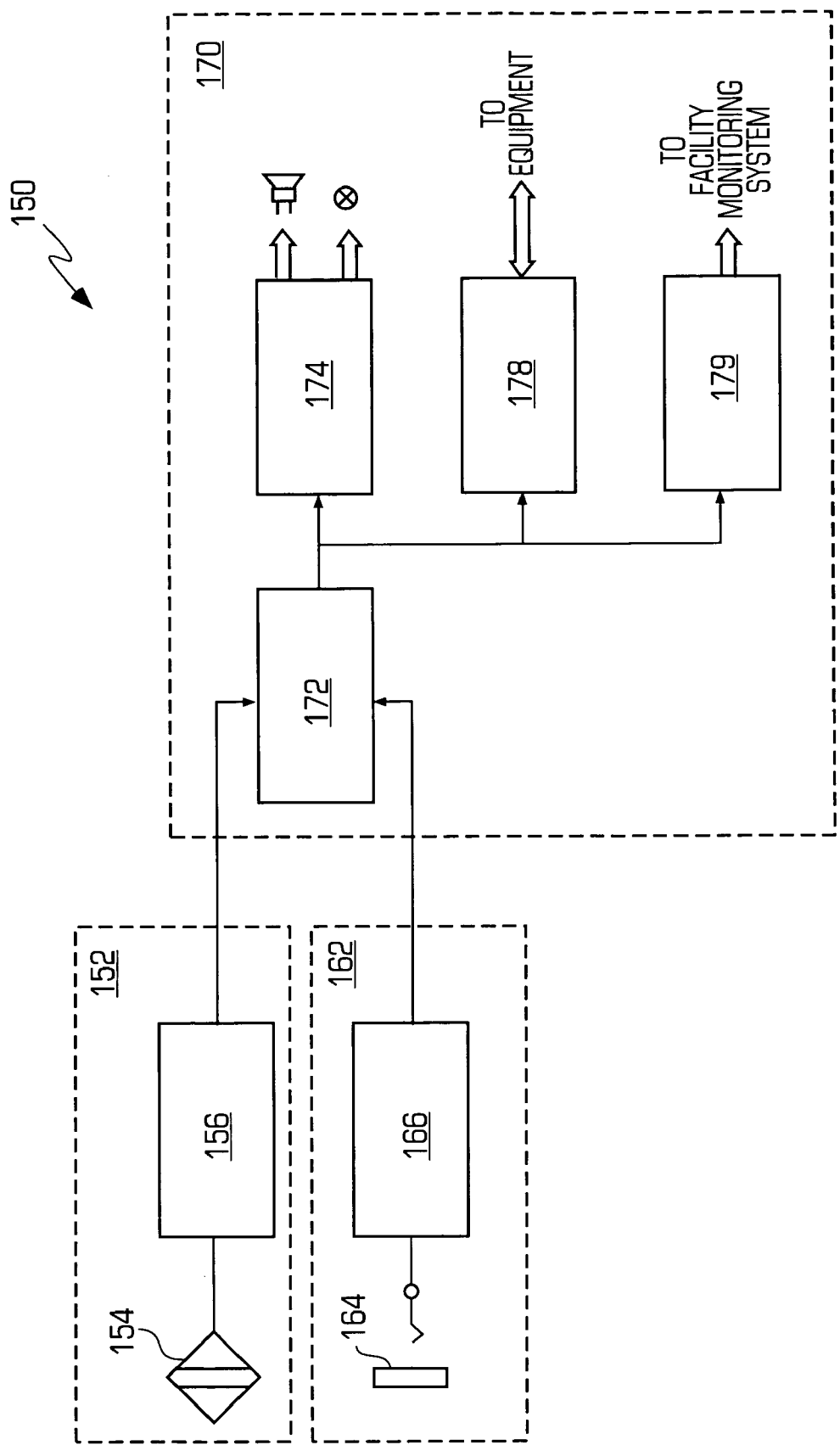
FIG. 8 depicts a generalized block diagram of an enhanced grounding system in accordance with the invention.

While the grounding system 60 provides numerous advantages over the currently used system, it does not prevent an operator from forgetting to ground himself or alert the operator if the fastening mechanism accidentally becomes disengaged. The grounding system 60 above cannot distinguish between a potentially dangerous situation where the operator forgets to use the grounding device 20 from a safe situation where the operator has gone home. In order to distinguish the potentially dangerous situation from the safe situation, it is desirable to determine not only whether the grounding device 20 is in use but also whether the operator is in the designated area. FIG. 8 depicts an enhanced grounding system 150 that monitors whether the grounding device 20 is in use and even determines whether the grounding device 20 should be in use. An alarm signal may be triggered if the operator is on the premises without being properly grounded. In addition, a signal can be issued to equipment to halt its operation should an ungrounded operator attempt access to sensitive components or a sensitive area.

FIG. 8 depicts a generalized block diagram of the enhanced grounding system 150 in accordance with the invention. The grounding system 150 includes a proximity sensing unit 152, a grounding device monitoring unit 162, and a base unit 170. The proximity sensing unit 152, which senses whether the operator is in a designated area, includes a proximity sensor 154 and, if desired/needed, a circuit 156. The proximity sensor 154 may be implemented by any device(s) deemed suitable by a person of ordinary skill in the art, such as an infrared motion detector, an ultrasonic proximity sensor, a microwave proximity sensor, a light barrier, or a mechanical detection means using a pressure mat. The circuit 156 transforms the output of the proximity sensor 154 to provide enabling signals to a logic circuit 172 in the base unit 170. In one embodiment, the grounding device monitoring unit 162 and/or the base unit 170 remain in a stand-by mode or a disabled mode until the proximity sensing unit 152 senses that the operator is in the designated area. In response to sensing operator presence, the grounding device monitoring unit 162 and/or the base unit 170 become enabled. In another embodiment, just the alarm may remain in a stand-by mode and become enabled upon detecting operator presence.

The grounding device monitoring unit 162, which monitors whether the grounding device 20 is in use, includes a detector 164. The detector 164 may detect whether the wristband 22 is grounded, for example by implementing the arrangement shown below in FIGS. 13a and 13b. Like the proximity sensor 154, the probe 164 feeds information to the base unit 170. A wristband monitoring circuit 166 may be incorporated into the grounding device monitoring unit 162 to properly process the probe reading for the base unit 170. The grounding device monitoring unit 162 may also incorporate information about whether the wristband 22 is worn properly, for example by reading the difference between the two wires in the device of FIGS. 14a–14c. The wrist strap monitoring circuit 166 may be of any construction deemed suitable by a person of ordinary skill in the art, as long as it provides pass/fail signals indicating whether the operator is wearing the wristband properly.

A logic circuit 172 in the base unit 170 processes the signal from the proximity sensing unit 152 and the signal from the grounding device monitoring unit 162 to determine if an alarm needs to be issued. An alarm circuit 174 is triggered only if the signal from the proximity sensing unit 152 indicates that the operator is in the designated area and the grounding device monitoring unit 162 indicates that the grounding device 20 is not in use. The grounding device 20 is not in use if either the wristband 22 is not grounded or the wristband 22 is grounded but the operator is not wearing the wristband properly. The alarm could be in the form of light 175 and/or sound 176 signals. Optionally, a connection or signal may be provided to an equipment interface 178, which is connected to the equipment that requires the operator to be grounded. The equipment, upon receiving the signal from the equipment interface 178, may either halt the equipment operation and/or issue an additional alarm. A signal may also be forwarded to a facility monitoring system 179, which maintains a log of when the alarm was issued. Although this particular embodiment employs logic circuits, the invention is not limited to logic circuit embodiments and the same function can be performed by other arrangements (e.g., a microcontroller) without departing from the spirit of the invention.

Figure 9A:
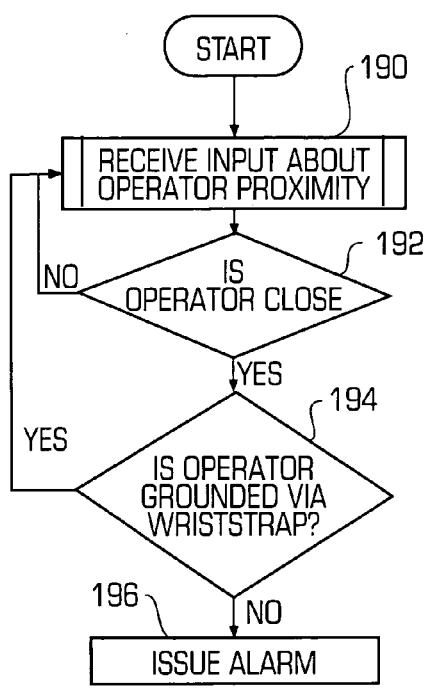
FIGS. 9a and 9b are flowcharts depicting the basic operation of the base unit in the ground monitoring system.

FIG. 9a is a flowchart depicting the basic operation of the base unit 170 in the ground monitoring system 150. As the flowchart shows, the base unit 170 receives input from the proximity sensing unit 152 regarding whether the operator is in the designated area (stage 190). If the operator is in the designated area (stage 192), the base unit 170 checks if the operator is grounded (stage 194). If the operator is not grounded, then an alarm is triggered (stage 196). The alarm is not triggered if either the operator is not in the designated area or the operator is in the designated area and properly grounded. The operator is properly grounded when the wristband 22 is grounded and making proper contact with the operator. When no alarm is issued, the base unit 170 waits a predetermined period of time, and restarts the process at stage 190.

Figure 9B:
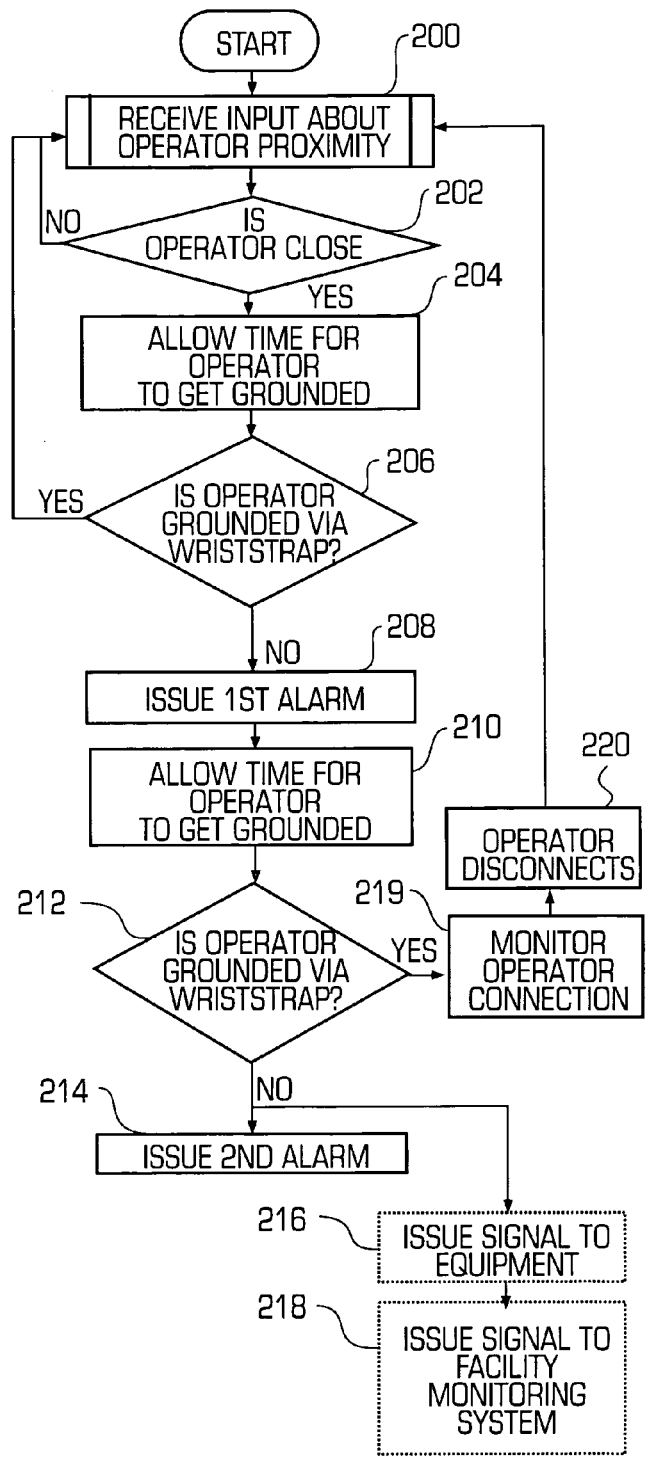

FIG. 9b is a flowchart depicting the detailed operation of the base unit 170. Unlike the process of FIG. 9a, this process takes into account the time it takes an operator to get grounded once he enters the designated area. In this process, after sensing the presence of the operator in the designated area, the base unit 170 waits a certain amount of time before checking if the operator is grounded. If the operator is not grounded at the end of the grace period, the alarm is triggered.

Referring to the flowchart in FIG. 9b, the base unit 170 receives input from the proximity sensing unit 152 regarding whether the operator is in the designated area (stage 200). If the operator is in the designated area (stage 202), the base unit 170 waits a predetermined grace period for the operator to get grounded (stage 204). At the end of the grace period, the base unit 170 checks if the operator is grounded (stage 206) and triggers the alarm (stage 208) if the operator is not grounded. After the alarm, the base unit 170 waits for another predetermined period of time (stage 210) before checking again to see if the operator has been grounded. If the operator is still not grounded, the alarm is triggered again (stage 214). Optionally, at this point, a signal may be issued to the equipment (stage 216), for example to enable/disable the equipment so that the operator cannot operate the equipment without first grounding himself. A signal may also be sent to the facility monitoring system (stage 218) so that the fact that the alarm was triggered can be logged. Information regarding the proximity and status of the operator may be provided to the facility monitoring equipment. If the operator grounded himself after the first alarm (stage 212), then the base unit 170 monitors the connection (stage 219). Once it is detected that the grounding device 20 is no longer in use (stage 220), the process starts over.

In one embodiment, the first alarm that is issued in stage 208 may be in a form of temporally spaced bursts of sound and/or light. The frequency of the alarm bursts may gradually increase until it reaches the frequency level that is associated with the second alarm of stage 214. FIG. 9c, which shows the alarm signal intensity as a function of time, visually depicts the change in frequency. While FIG. 9c depicts the case where the operator does not ground himself after the first alarm, FIG. 9d depicts the case where the operator grounds himself after the first alarm, preventing the beeping/flashing frequency from increasing to the level of the second alarm. The alarm stops when the operator properly grounds himself. If the wristband 22 accidentally becomes disengaged from the grounding jack, the base unit 170 would detect the disengagement in stage 220 and issue the alarm in stage 208. In some embodiments, the alarm cycle repeats (first alarm, then second alarm) until either operator grounds himself or leaves the area.

Figure 10:
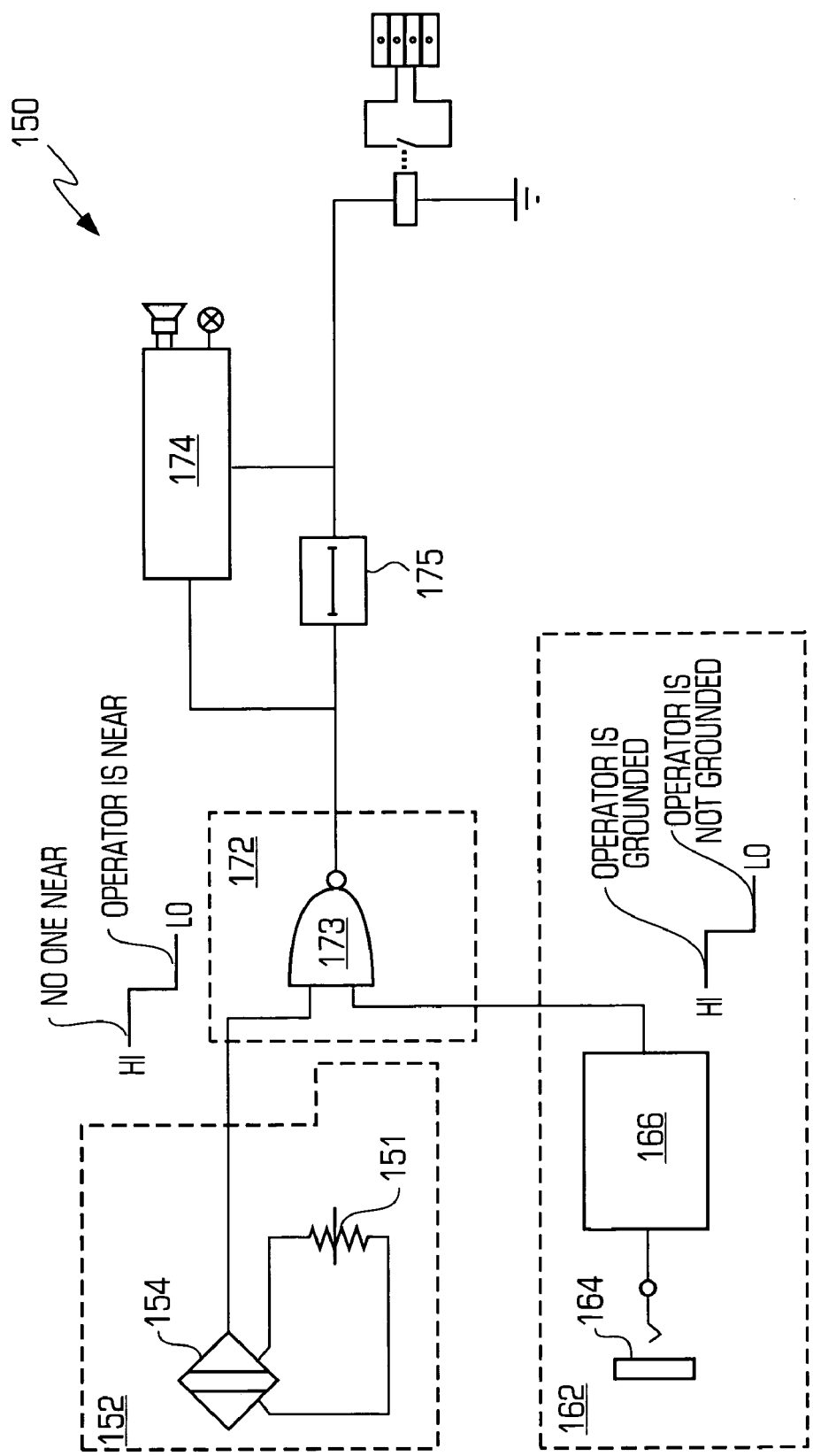
FIG. 10 depicts the enhanced grounding system in accordance with one embodiment of the invention.

FIG. 10 depicts the enhanced grounding system 150 in accordance with one embodiment of the invention. In the particular embodiment that is shown, the proximity sensing unit 152 is implemented with an infrared pyrosensor (motion detector) combined with optional sensitivity adjustment device 151 (e.g., a means for continuous adjustment such as a tuner or a potentiometer, or alternatively, a switch), which a person of ordinary skill in the art would know how to implement. The motion detector may be an infrared motion detector, an infrared proximity sensor, a microwave proximity detector, an ultrasonic proximity detector, a light barrier, or a mechanical detecting mechanism. If a motion is detected, the proximity sensing unit 152 outputs a low signal; if no motion is detected, it outputs a high signal. The grounding device monitoring unit 162 outputs a low signal if the operator is not grounded and a hi signal if the operator is grounded. The logic circuit 172 of the base unit 170 includes an a NAND gate 173 that is designed to trigger an alarm only if both the signal from the proximity sensing unit 152 and the signal from the grounding device monitoring unit 162 are low. The base unit 170 also includes a time delay unit 175 that gives the operator a grace period to get grounded.

Figure 11:
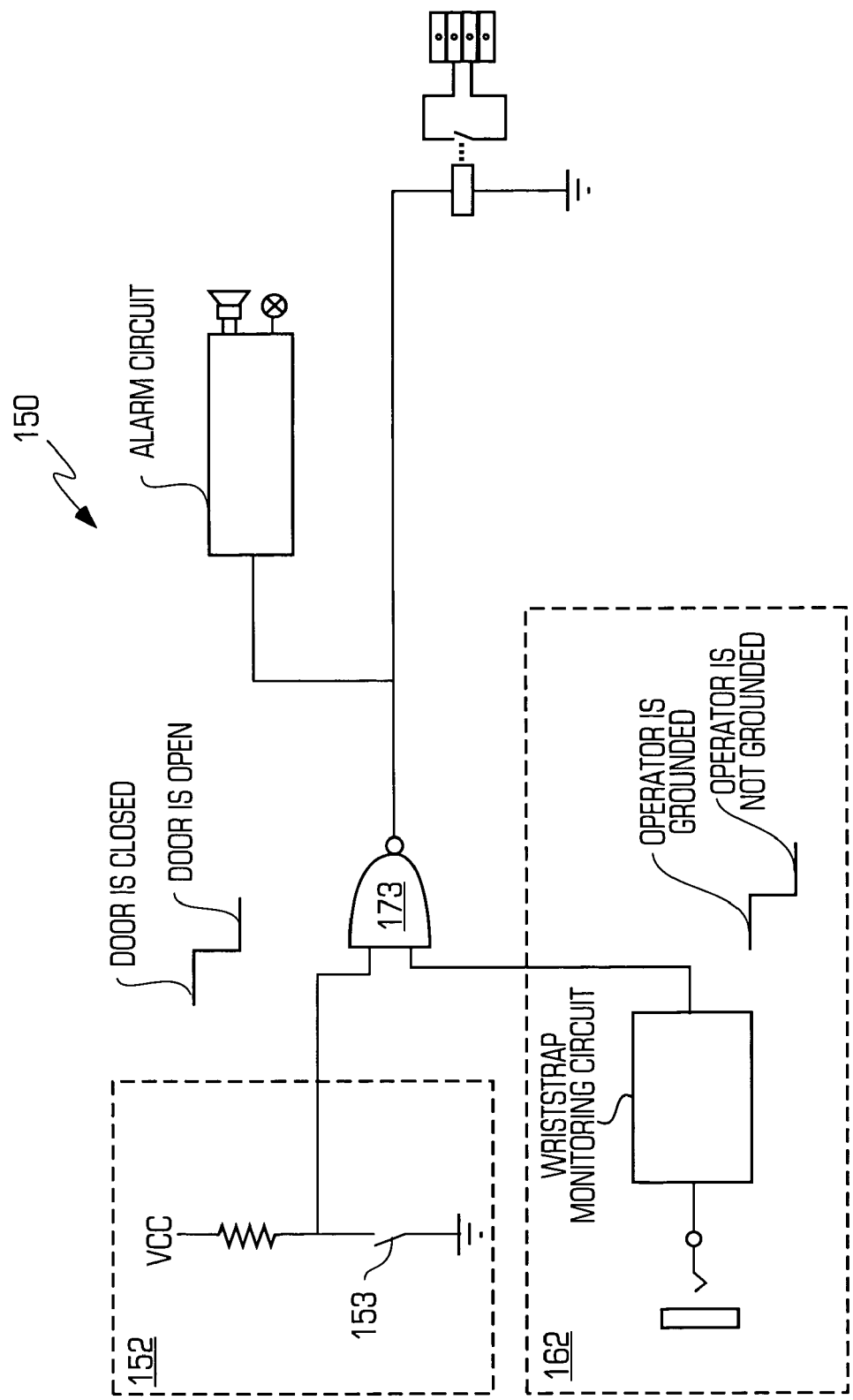
FIG. 11 depicts the enhanced grounding system in accordance with another embodiment of the invention.

FIG. 11 depicts the ground monitoring system 150 in accordance with another embodiment of the invention. This embodiment is similar to the embodiment of FIG. 10, with the main difference being that the proximity sensing unit 152 includes a safety access switch 153 for various equipments (such as access hatch, door, etc.) instead of the motion detector 154. The switch 153 does not permit use of the equipment until the switch is closed. In this embodiment, a time delay unit may not be necessary since an operator must be grounded prior to gaining access to the equipment.

Figure 12:
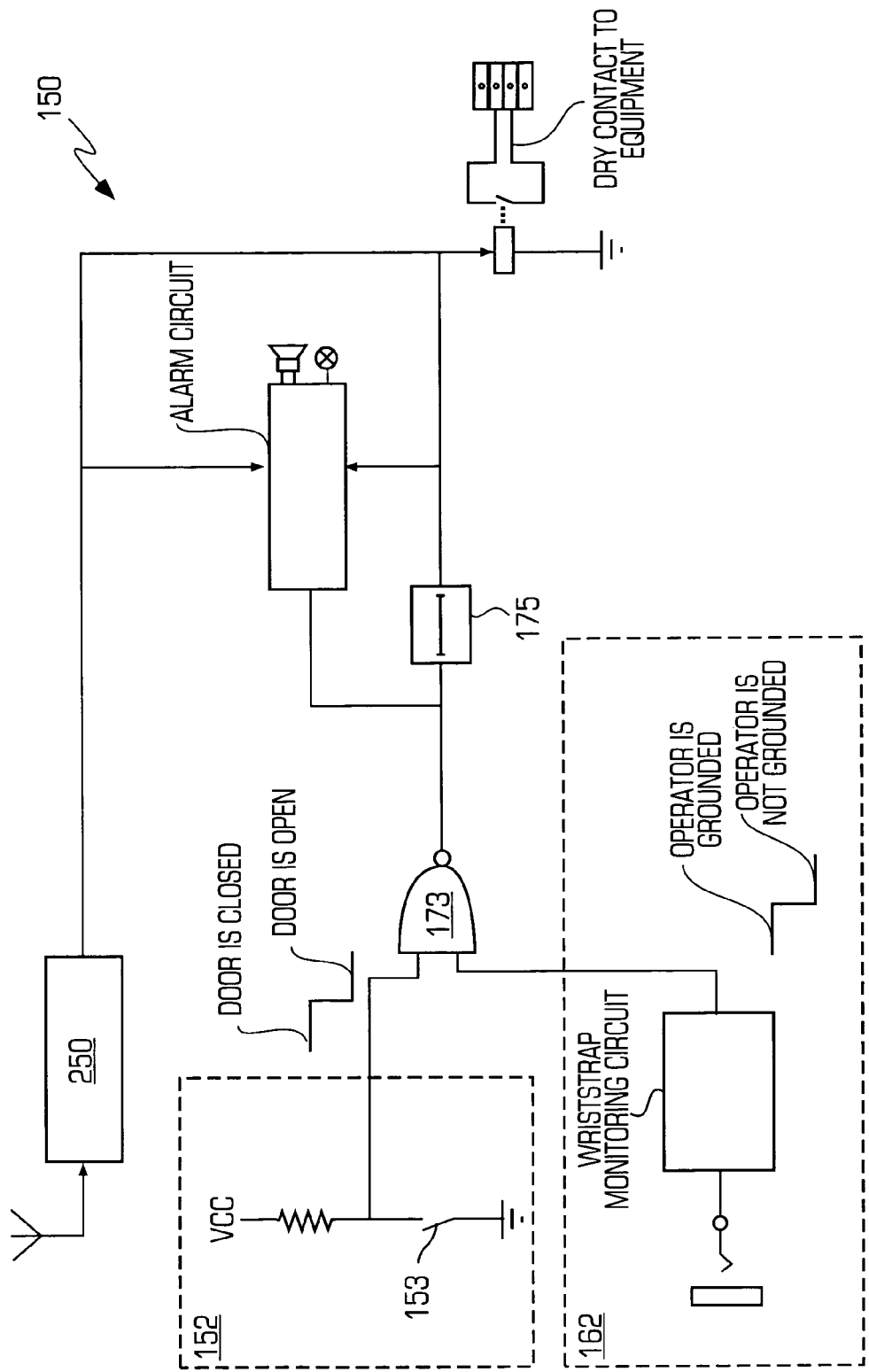
FIG. 12 depicts the enhanced grounding system in accordance with yet another embodiment of the invention.

FIG. 12 depicts the enhanced grounding system 150 in accordance with yet another embodiment of the invention. This embodiment is similar to the embodiment of FIG. 11 combined with an electrostatic voltage sensor 250 that restricts access to equipment if electrostatic voltage is present, providing an extra layer of protection. With this embodiment, if an operator brings a charged object to the equipment, the alarm will be triggered and/or access to the equipment will be denied until the charge is dissipated even if the operator is properly grounded. Electrostatic voltage sensor may be of any available construction, such as EM Aware ESD monitor by Credence Technologies (ftp://credencetech.com/pub/credence/EMAware.pdf).

Figure 13B:
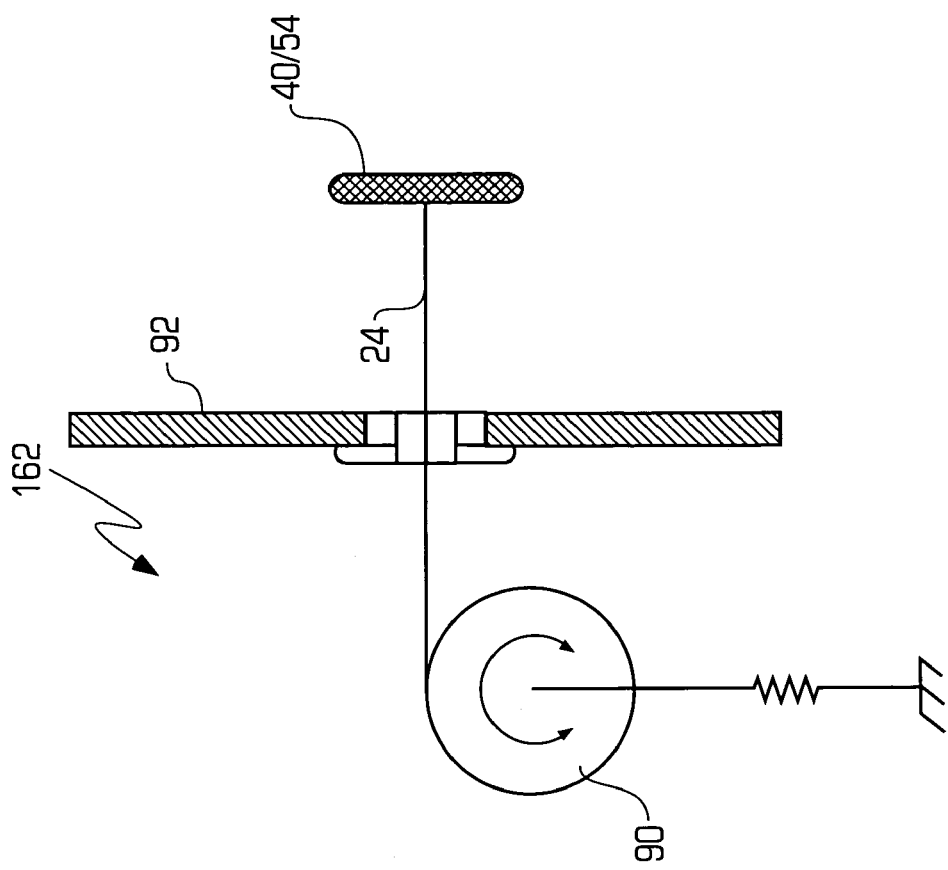
FIGS. 13a and 13b depict one embodiment of the grounding device monitoring unit in accordance with the invention.
Figure 13A:
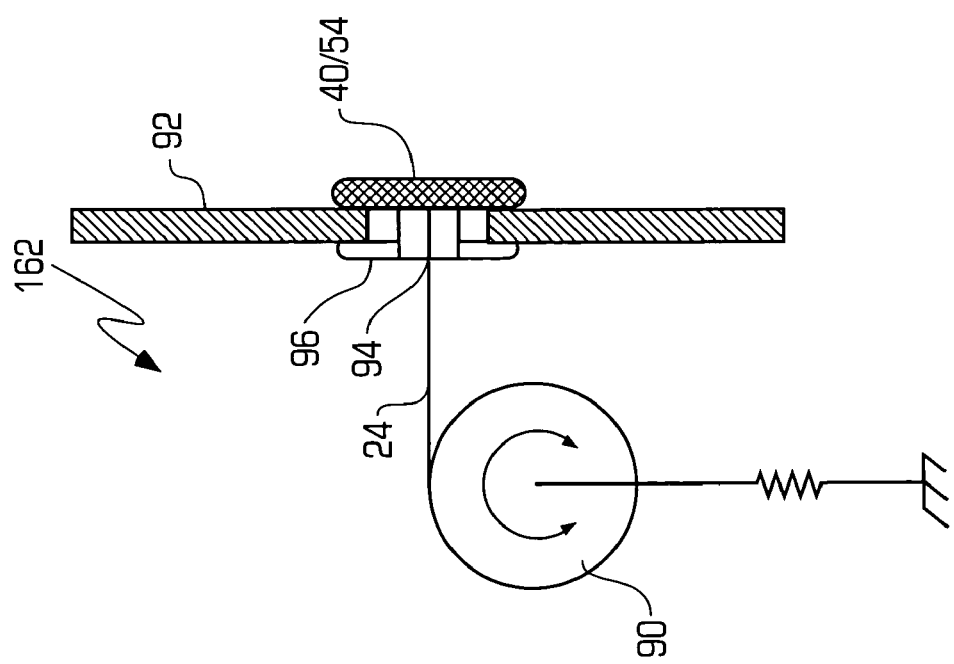

FIGS. 13a and 13b depict one embodiment of the grounding device monitoring unit 162 in accordance with the invention. This grounding device monitoring unit 162 monitors the voltage difference between a conductive plate 92 and a grounded rotating device 90. The grounded rotating device 90 may be the spring-loaded spool 70 (see FIG. 5a), the pulley 86 (see FIG. 7), or another device. The conductive plate 92, which may be the cover of a piece of equipment, has a hole 94 through which the coupling mechanism 24 extends to contact the grounded rotating device 90. There is an insulating region 96 that separates the hole 94 from the conductive plate 92. The grounded rotating device 90 is electrically coupled to the magnetic mating structure 40 (which may alternatively be a mechanical mating structure 54) through the coupling mechanism 24. When the grounding device 20 is in use, as shown in FIG. 13b, the conductive plate 92 is not electrically coupled to the grounded rotating device 90. However, when the grounding device is not in use, the grounded rotating device 90 retracts the coupling mechanism 24 to the point where the magnetic mating structure 40 contacts the conductive plate 92. When the magnetic mating structure 40 contacts the conductive plate 92, the conductive plate 92 also becomes grounded. Thus, by monitoring whether the conductive plate 92 is grounded or not, the grounding device monitoring unit 162 can tell if the grounding device 20 is in use.

FIG. 14a shows an end view/cross section of embodiment of a magnetic mating structure 40 in accordance with the invention. The magnetic mating structure 40 includes an outer conductive ring 102 and an inner conductive ring 104 separated by an insulating region 106. Inside the inner conductive ring 104 is a magnetic material 108, although the specific location of the magnetic material 108 is not a limitation of the proposed invention. As shown in FIG. 14b, the magnetic mating structure 40 is mated with a ferromagnetic device 110, which also has an outer conductive ring 112 and an inner conductive ring 114 with an insulating region 116 between the two rings. Inside the inner conductive ring 114 is a ferromagnetic material 118. Preferably, the ferromagnetic device 110 has similar dimensions as the magnetic mating structure 40 so that the two parts can be mated easily as shown in FIG. 14c.

Since the outer conductive ring 102 is electrically insulated from the inner conductive ring 104 and the outer conductive ring 112 is electrically insulated from the inner conductive ring 114, it is possible to use up to two sets of two coupling mechanisms 24 with this embodiment. When the magnetic mating structure 40 is mated with the ferromagnetic device 110, each of the coupling mechanisms 24a mates with one of the coupling mechanisms 24b, creating two terminals. By monitoring the electrical continuity between the inner-ring terminal that connects a first set of coupling mechanisms 24a and 24b and the outer-ring terminal that connects a second set of coupling mechanisms 24a and 24b, it can be determined whether the operator is properly grounded. Electrical continuity between the two terminals indicates that the wristband is electrically coupled to the wearer. Thus, the embodiment of FIGS. 14a–14c help detect a situation where the user is wearing the wristband incorrectly so that the wristband is not making proper electrical contact with the user. This embodiment of the magnetic mating structure 40 may be used in the grounding device monitoring unit 162 of FIG. 13a and FIG. 13b. The configuration of the magnetic mating structure 40 and the ferromagnetic device 110 shown here provide the additional benefit of being difficult to break/damage.

A shell 109 that supports the magnetic mating structure 40 contacts a shell 119 that supports the ferromagnetic device. The shells 109 and 119 may be electrically conductive, depending on the embodiment. A person of ordinary skill in the art would understand that other devices may be used to detect whether the wristband 22 is worn properly, such as the single-wire device Jewel™ made by Desco, and any of these devices may be used to implement the grounding device monitoring unit 162.

Figure 15A:
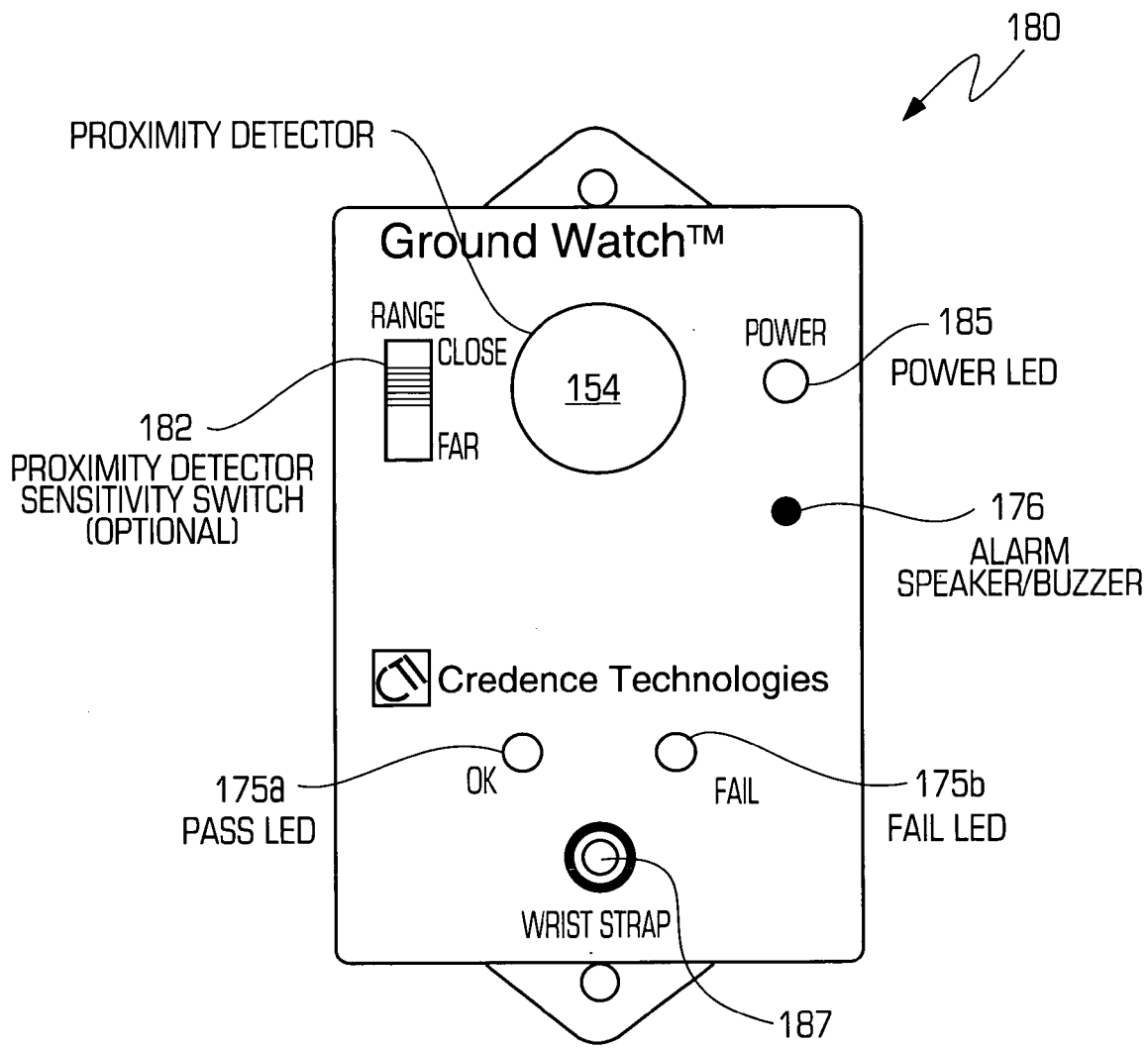
FIGS. 15a and 15b depicts a user interface device that may be used for the enhanced grounding system in accordance with the invention.

FIG. 15a depicts a user interface device 180 that may be used for the enhanced grounding system 150 in accordance with the invention. The user interface device 180 includes a connector 181 through which the wristband 22 is coupled to the grounded object 30. This connector 181 could be of one of the magnetic/mechanical configurations described above or any other conventional configurations. The user interface device 180 further includes the proximity detector 154 and a switch/tuner 182 for adjusting the sensitivity of the proximity detector 154. There is also a pass LED 175a and a fail LED 175b and a speaker or a buzzer 176 that are used to alert the operator (see, e.g., stages 208 and 214 in FIG. 9b) that he needs to ground himself.

Figure 15B:
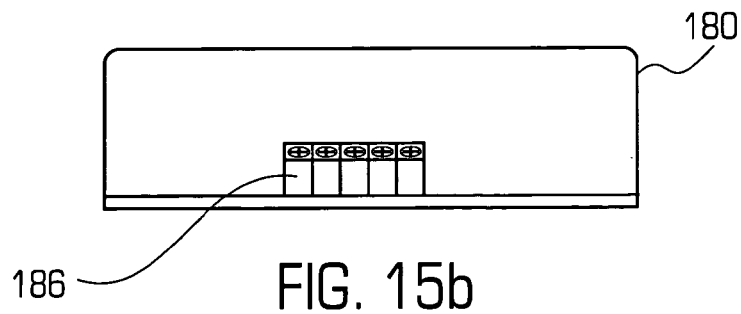

FIG. 15b depicts a connecting mechanism 186, which may be a terminal block or a connector, that provides power to the user interface device 180 and also provides output to various equipment. A power LED light 185 (see FIG. 15a) indicates whether the user interface device 180 is connected to the connecting mechanism 186.

For operators, it is often important to be free of constraints while wearing the grounding device 20. Conventional grounding devices tend to limit operator movements because of the coupling mechanism that freely hangs from the wristband. The hanging coupling mechanism that interferes with movement provides one more reason for operators to not properly ground themselves.

Figure 16B:
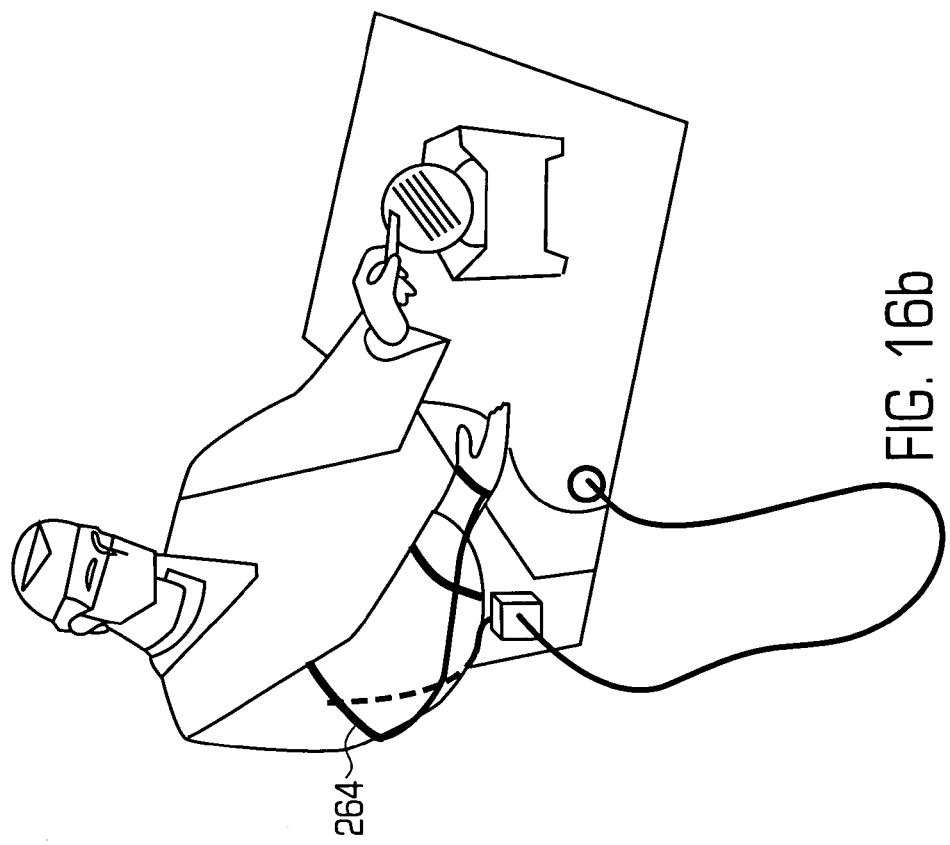
FIGS. 16a and 16b depict a method and system for grounding the operator with minimum movement restriction in accordance with the invention.
Figure 16A:
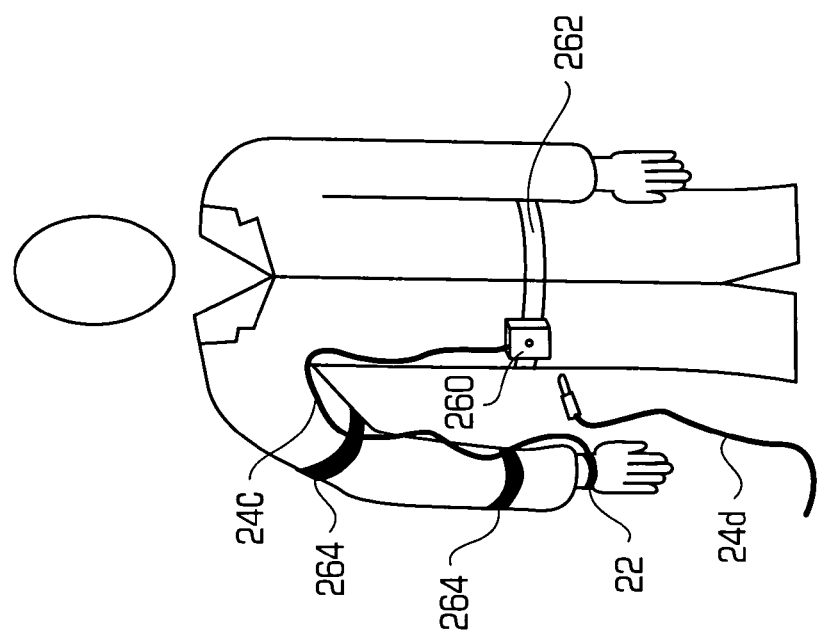

FIGS. 16a and 16b depict a method and device for grounding the operator with minimum movement restriction in accordance with the invention. As shown in FIG. 16a, the operator wears a wristband 22 that is connected to the coupling mechanism 24. The coupling mechanism 24 is channeled either over or under the operator's garment and couples to a connector 260. The connector 260 connects a first section 24c of the coupling mechanism that extends from the wristband 22 to a second section 24d of the coupling mechanism that extends from the grounded object 30, and may be worn in a way that does not limit the operator's movements. For example, as shown in FIG. 16a, the connector 260 may be attached to a belt 262. The connector 260 may be designed so that either the first section 24c or the second section 24d, or both, may be unplugged from it. As shown in FIG. 16b, one or more garters 264 may be worn around the arm to keep the first section 24c of the coupling mechanism close to the body so that the hanging coupling mechanism is unlikely to interfere with the operator's activity. As described above, the coupling mechanism 24 can be automatically retracted (e.g., by a spool) once the operator disengages the fastening device. A spool may be incorporated into the connector 260.

FIG. 16b depicts an operator working while wearing the grounding device 20 of FIG. 16a. As shown, the grounding device 20 does not impede the operator's movements.

While the foregoing has been with reference to a particular embodiment of the invention, it will be appreciated by those skilled in the art that changes in this embodiment may be made without departing from the principles and spirit of the invention, the scope of which is defined by the appended claims.

What is claimed is:

1. A wearable grounding device that grounds a wearer, the grounding device comprising a wristband that is electrically coupled to a grounded object with a fastening mechanism, wherein the fastening mechanism automatically releases to separate the wristband from the grounded object in response to a force applied to the fastening mechanism and the fastening mechanism further comprises a magnetic coupling mechanism and a coupling mechanism adjacent to and electrically separated from the magnetic coupling mechanism wherein the magnetic coupling mechanism and the coupling mechanism are both coupled to the grounded object if the wristband properly contacts the wearer.

2. The device of claim 1, wherein the fastening mechanism comprises a magnetic mating structure and a ferromagnetic fixing mechanism that releasably couple to each other.

3. A wearable grounding device that pounds a wearer, the grounding device comprising a wristband that is electrically coupled to a grounded object with a fastening mechanism, wherein the fastening mechanism automatically releases to separate the wristband from the grounded object in response to a force applied to the fastening mechanism and the fastening mechanism comprises a magnetic material partially surrounded by a first conductive ring, wherein the magnetic material releasably couples to a ferromagnetic material that is partially surrounded by a second conductive ring so that the first and the second conductive rings contact each other, a coupling mechanism connected to at least one of the first and the second conductive rings, a third conductive ring arranged concentrically with the first conductive ring and electrically separated from the first conductive ring, a fourth conductive ring arranged concentrically with the second conductive ring and electrically separated from the second conductive ring so that the third conductive ring and the fourth conductive ring contact each other when the magnetic material attaches to the ferromagnetic material, wherein the third conductive ring and the fourth conductive ring become electrically coupled if the wristband properly contacts the wearer, and a second coupling mechanism connected to at least one of the third and the fourth conductive rings.

4. The device of claim 1, wherein the fastening mechanism comprises:
   a coupling mechanism with a magnetic mating structure attached to at least one end; and
   a ferromagnetic surface to which the magnetic mating structure is release ably connected.

5. The device of claim 4, wherein the magnetic mating structure detaches from the ferromagnetic device if a tension level in the coupling mechanism exceeds a threshold value.

6. The device of claim 1, wherein the fastening mechanism comprises;
   a coupling mechanism with a ferromagnetic fixing mechanism attached to at least one end; and
   a magnetic mating structure to releasably connected to the ferromagnetic fixing mechanism.

7. The device of claim 6, wherein the magnetic properties of the magnetic mating structure is such that the magnetic mating structure detaches from the ferromagnetic fixing mechanism if a tension level in the cable exceeds a threshold value.

8. The device of claim 1, wherein one of the grounded abject and the wristband is integrated with the fastening mechanism.

9. The device of claim 1, wherein the fastening mechanism comprises a hook-type mating structure that releasably couples to a loop-type fixing mechanism.

10. The device of claim 1, wherein the fastening mechanism comprises a spring-release fixing mechanism and a mechanical mating structure that are releasably coupled to each other.

11. The device o f claim 1, wherein the wristband is electrically coupled to the grounded object with a coupling mechanism that is refracted in by a rotating device if the fastening mechanism is released.

12. The device o f claim 11, wherein the rotating device is integrated with the wristband.

13. The device o f claim 11, wherein the rotating device comprises a pulley that translates a first force exerted by a weight at one end of the coupling mechanism into a retraction of the coupling mechanism.

14. A system for grounding an operator, the system comprising:
   a wristband;
   a grounded object that is electrically connected to the wristband with a fastening mechanism that includes a coupling mechanism, wherein the fastening mechanism releases to separate the wristband from the grounded object if a tension level in the coupling mechanism exceeds a threshold level, and a rotating device that retracts the coupling mechanism after the fastening mechanism is released wherein the rotating device is driven by an electric motor.

15. The system of claim 14, wherein the rotating device maintains a constant level of tension in the coupling mechanism, the rotating device further comprising a latch that prevents the coupling mechanism from being refracted when the fastening mechanism is not released.

16. The system of claim 14, wherein the rotating device comprises a spring-loaded spool.

17. A system for grounding an operator, the system comprising:
   a wristband;
   a grounded object that is electrically connected to the wristband with a fastening mechanism that includes a coupling mechanism, wherein the fastening mechanism releases to separate the wristband from the grounded object if a tension level in the coupling mechanism exceeds a threshold level, and mechanism is attached to a mating structure and a second end of the coupling mechanism is attached to a weight, the system further comprising:
   a wall having a hole through which the coupling mechanism extends so that the weight and the mating structure are located on different sides of the wall; and
   a rotating device located to pull the coupling mechanism toward the wall when the fastening mechanism is released, in response to a force exerted by the weight at the second end of the coupling mechanism, until the mating structure contacts the wall.

18. The system of claim 17 wherein the grounded object is a part of the rotating device and the mating structure is electrically connected to the grounded object through the coupling mechanism, the system further comprising:
   an electrically conductive section of the wall that is separated from the hole by an insulating region, wherein the electrically conductive section is located to contact the mating structure only when the mating structure contacts the wall; and
   a grounding device monitoring unit that monitors a voltage difference between the grounded object and the electrically conductive section to determine whether the wristband is grounded.

19. The system of claim 18 further comprising a proximity sensing unit for sensing whether the wristband is in a designated area.

20. The system of claim 19 wherein the proximity sensing unit comprises at least one of: an infrared motion detector, an infrared proximity sensor, a microwave proximity detector, an ultrasonic proximity detector, a light barrier, and a mechanical detecting means.

21. The system of claim 19 wherein the proximity sensing unit comprises a sensitivity adjustment mechanism.

22. The system of claim 19 further comprising a logic circuit that receives input from both the grounding device monitoring unit and the proximity sensing unit and triggers an alarm only if the proximity sensing unit indicates that the wristband is in the designated area and the grounding device monitoring unit indicates that the wristband is not grounded.

23. The system of claim 22 wherein the alarm comprises a sequence of signals that are activated at a preset frequency, further comprising a circuit for changing the frequency.

24. The system of claim 22 further comprising a facility monitoring system interface unit for logging the alarm in a facility database if the proximity sensing unit indicates that the wristband is in the designated area and the grounding device monitoring unit indicates that the wristband is not grounded.

25. The system of claim 19 further comprising an equipment interface unit for disabling an equipment if the proximity sensing unit indicates that the wristband is in the designated area and the grounding device monitoring unit indicates that the wristband is not grounded.

26. The system of claim 19 further comprising a time delay unit for delaying a triggering of the alarm by a predetermined grace period.

27. The system of claim 19 further comprising a static voltage detection mechanism.

28. A system for grounding an operator, the system comprising a proximity sensing unit for sensing operator presence in a designated area, the proximity sensing unit enabling one or more of a grounding device monitoring unit and a logic circuit in response to sensing operator presence, wherein the grounding device monitoring unit monitors whether the operator is electrically grounded and the logic circuit triggers an alarm if the proximity sensing unit indicates that the operator is in the designated area and the grounding device monitoring unit indicates that the wristband is not rounded.

29. The system of claim 28 wherein the proximity sensing unit comprises at least one of: an infrared motion detector, an infrared proximity sensor, a microwave proximity detector, an ultrasonic proximity detector, a light barrier, and a mechanical detecting means.

30. The system of claim 28 wherein the proximity sensing unit comprises a sensitivity adjustment mechanism.

31. The system of claim 30 wherein the sensitivity adjustment mechanism comprises one of a means for continuous adjustment and a switch.

32. The system of claim 31 wherein the alarm comprises a sequence of signals that are activated at a preset frequency, further comprising a circuit for changing the frequency.

33. The system of claim 31 further comprising a facility monitoring system interface unit for logging the alarm in a facility database if the proximity sensing unit indicates that the wristband is in the designated area and the grounding device monitoring unit indicates tat the operator is not grounded.

34. The system of claim 28 further comprising an equipment interface unit for disabling an equipment if the proximity sensing unit indicates tat the operator is in the designated area and the grounding device monitoring unit indicates that the operator is not grounded.

35. The a system of claim 28 further comprising a time delay unit for delaying a triggering of the alarm by a predetermined grace period.

36. The system of claim 28 further comprising a static voltage detection mechanism.

37. The system of claim 28, wherein the proximity sensing unit further comprises an electromagnetic radiation sensing device.

38. The system of claim 37, wherein the electromagnetic radiation sensing device further comprises an optical sensing device.

39. A method of grounding an operator, the method comprising electrically coupling a wristband to a grounded object with a fastening mechanism that includes a coupling mechanism, wherein the fastening mechanism automatically disengages when a tension level in the coupling mechanism exceeds a threshold level;
retracting the coupling mechanism with a rotating device when the fastening mechanism is released:
monitoring a voltage difference between the grounded object and another object that becomes grounded only when the coupling mechanism is retracted; and
determining that the wristband is not grounded when the voltage difference is approximately zero.

40. The method of claim 39, wherein electrically coupling the wristband to the grounded object comprises attaching a magnetic mating structure to a ferromagnetic fixing mechanism.

41. The method of claim 39, w herein electrically coupling the wristband to the grounded object comprises mechanically mating a mating structure with a spring-release fixing mechanism.

42. The method of claim 39 further comprising:
sensing whether the wristband is in a designated area; and
triggering an alarm if the wristband is in the designated area and the voltage difference is approximately zero.

43. The method of claim 42 wherein the alarm comprises a sequence of signals released at a predetermined frequency, further comprising changing the frequency.

44. The method of claim 42 further comprising waiting a predetermined period of time before triggering the alarm.

45. The method of claim 42 further comprising disabling an equipment if the wristband is not grounded.

46. The method of claim 39 further comprising:
connecting the wristband to the grounded object with a first coupling mechanism and a second coupling mechanism, wherein the first coupling mechanism and the second coupling mechanisms are electrically connected to each other only if the wristband is worn properly to allow both coupling mechanisms to electrically connect to the wearer; and
monitoring electrical continuity between the first and the second coupling mechanisms to determine if the wristband is worn properly.

47. A method of grounding an operator, the method comprising:
sensing operator presence in a designated area;
if the operator is present in the designated area, monitoring a wristband to determine whether the operator is electrically grounded; and
triggering an alarm if the operator is not grounded.

48. A wriststrap used to connect a wearer to a grounded object the wriststrap further comprising a conductive stray coupled to a first end of a conductive portion and a magnetic mating surface attached to a second end of the conductive portion wherein the magnetic mating surface magnetically fastens the wriststrap to a grounded object to maintain electrical contact between the wriststrap and the grounded object.

49. The wriststrap of claim 48, wherein the magnetic mating surface automatically releases to separate the wriststrap and the conductive portion from the grounded object in response to a force applied to the magnetic mating surface.

50. A wriststrap used to connect a wearer to a grounded object, the wriststrap further comprising a conductive strap coupled to a first end of a conductive portion and a ferromagnetic mating surface attached to a second end of the conductive portion wherein the ferromagnetic mating surface fastens the wriststrap to a grounded object to maintain electrical contact between the wriststrap and the grounded object.

51. The wriststrap of claim 50, wherein the ferromagnetic mating surface automatically releases to separate the wriststrap and the conductive portion from the grounded object in response to a force applied to the ferromagnetic mating surface.

52. A cord that is used for a wearable grounding device comprising a first portion with a first end coupled to a conductive cuff and a magnetic mating element attached to a second end of the first portion wherein the magnetic mating element is capable of magnetically fastening the a conductive cuff to a grounded object to maintain electrical contact between the conductive cuff and the grounded object.

53. The cord of claim 52, wherein the magnetic mating element automatically releases to separate the conductive cuff from the grounded object in response to a force applied to the magnetic connector.

54. A cord that is used for a wearable grounding device comprising a first portion with a first end coupled to a conductive cuff and a ferromagnetic mating clement connector attached to a second end of the first portion wherein the ferromagnetic mating element is capable of magnetically fastening a conductive cuff to a grounded object to maintain electrical contact between the conductive cuff and the grounded object.

55. The cord of claim 54, wherein the ferromagnetic mating element automatically releases to separate the conductive cuff from the grounded object in response to a force applied to the ferromagnetic mating element.

* * * * *